(12) United States Patent
Liu et al.

(10) Patent No.: US 9,095,589 B2
(45) Date of Patent: *Aug. 4, 2015

(54) CHIRALLY PURE ISOMERS OF ITRACONAZOLE FOR USE AS ANGIOGENESIS INHIBITORS

(75) Inventors: Jun O. Liu, Clarkesville, MD (US); Curtis R. Chong, Honolulu, HI (US); Jing Xu, Parkville, MD (US); Jun Lu, Monmouth JCT, NJ (US); Shridhar Bhat, Cockeysville, MD (US); Wie Shi, Fayetville, AR (US)

(73) Assignee: Johns Hopkins University, Baltimore, MD (US)

( * ) Notice: Subject to any disclaimer, the term of this patent is extended or adjusted under 35 U.S.C. 154(b) by 247 days.

This patent is subject to a terminal disclaimer.

(21) Appl. No.: 13/444,642

(22) Filed: Apr. 11, 2012

(65) Prior Publication Data

US 2013/0102614 A1 Apr. 25, 2013

Related U.S. Application Data

(63) Continuation-in-part of application No. 12/594,777, filed as application No. PCT/US2008/004513 on Apr. 7, 2008, now abandoned.

(60) Provisional application No. 60/922,059, filed on Apr. 5, 2007, provisional application No. 61/474,052, filed on Apr. 11, 2011.

(51) Int. Cl.
*A61K 31/496* (2006.01)
*A61K 31/4178* (2006.01)
*A61K 45/06* (2006.01)

(52) U.S. Cl.
CPC ............ *A61K 31/496* (2013.01); *A61K 31/4178* (2013.01); *A61K 45/06* (2013.01)

(58) Field of Classification Search
CPC . A61K 31/496; A61K 45/06; A61K 31/4178; A61K 2300/00
See application file for complete search history.

(56) References Cited

U.S. PATENT DOCUMENTS

| 4,267,179 A | 5/1981 | Heeres et al. |
| 4,616,027 A | 10/1986 | Richardson et al. |
| 5,474,997 A * | 12/1995 | Gray et al. ............... 514/254.07 |
| 6,166,018 A | 12/2000 | McCullough et al. |

FOREIGN PATENT DOCUMENTS

| WO | WO/2006/004795 | 12/2006 |
| WO | WO/2008/124132 A1 | 10/2008 |

OTHER PUBLICATIONS

Baker et al. Stereochemistry and drug efficacy and development: relevance of chirality to antidepressant and antipsychotic drugs, Annals of Medicine (Stockholm, Sweden), 2002, 24 (7/8), 537-543.*
Chong, C. R. et al ., 'Inhibition of angiogenesis by the antifungal drug itraconazole', ACS Chemical Biology, 2007, vol. 2, No. 4, pp. 263-270.
International Search Report regarding PCT/US2013/036024, mailed: Jul. 26, 2013.
Zarn et al., "Azole Fungicides Affect Mammalian Steroidogenesis by Inhibiting Sterol 14α Demethylase and Aromatase", *Environmental Health Perspectives*, 111(3):255-261 (2003).
Shi et al., "Impact of Absolute Stereochemistry on the Antiangiogenic and Antifungal Activities of Intraconzale", *ACS Med Chem Lett* 1(4):155-159 (2010).

* cited by examiner

*Primary Examiner* — Gina Justice
*Assistant Examiner* — Genevieve S Alley
(74) *Attorney, Agent, or Firm* — DLA Piper LLP (US)

(57) ABSTRACT

Described herein are methods of inhibiting angiogenesis, and treating and preventing disorders associated with angiogenesis by administering anti-angiogenesis compounds to a subject.

9 Claims, 9 Drawing Sheets

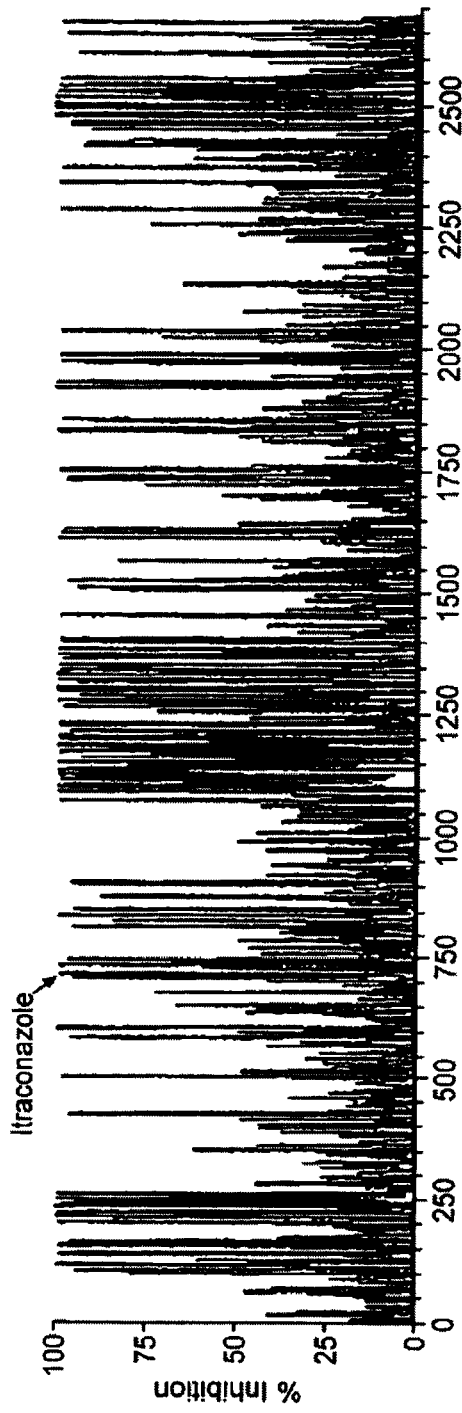
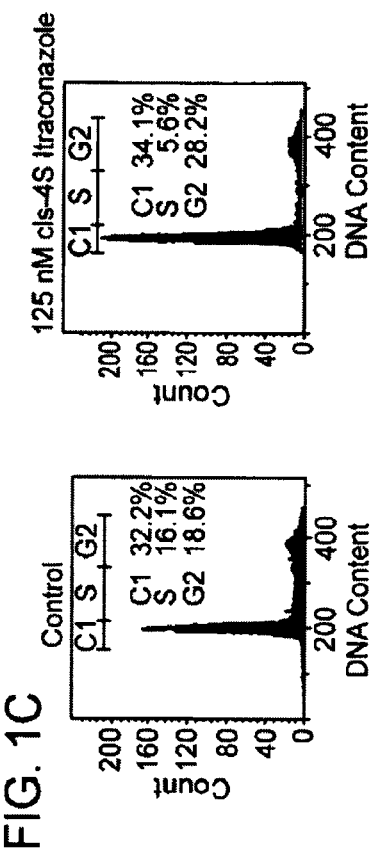
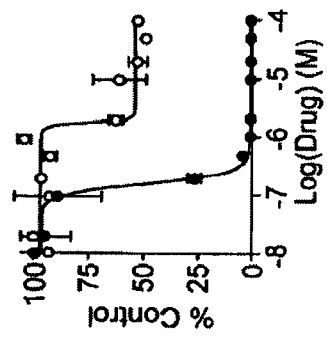
FIG. 1A
FIG. 1B
FIG. 1C

Chiral HPLC Analysis Data and Optical Rotation of Itraconazole Stereoisomers

| Compounds | | Retention time (min)$^\alpha$ | Diastereomeric purity | $[\alpha]\eta$ in $CHCl_3$ |
|---|---|---|---|---|
| Cis- | 23a(2S, 4R, 2'S) | 43.017 | >98% | - 5.5 |
| | 23d(2R, 4S, 2'R) | 42.520 | | + 5.7 |
| | 23b(2S, 4R, 2'R) | 46.333 | | - 12.3 |
| | 23c(2R, 4S, 2'S) | 42.547 | | + 12.6 |
| Trans- | 23e(2S, 4S, 2'S) | 38.933 | | - 13.2 |
| | 23h(2R, 4R, 2'R) | 39.573 | | + 13.3 |
| | 23f(2S, 4S, 2'R) | 37.800 | | - 19.1 |
| | 23g(2R, 4R, 2'S) | 39.253 | | + 18.6 |

FIG. 5

High-resolution mass spectrometry data

| Compounds | Calculated (M+H$^+$) (C$_{35}$H$_{39}$Cl$_2$N$_8$O$_4$) | Found |
|---|---|---|
| 23a | 705.2471 | 705.2458 |
| 23b | | 705.2455 |
| 23c | | 705.2476 |
| 23d | | 705.2458 |
| 23e | | 705.2455 |
| 23f | | 705.2459 |
| 23g | | 705.2474 |
| 23h | | 705.2456 |

FIG. 6

Potency of Itraconazole Stereoisomers in Biological Assays

| Compounds | HUVEC | | S.cerevisiae (BY4741) | | C.albicans (10261) | | C.neoformans (H99) | | C.glabrata | | | |
|---|---|---|---|---|---|---|---|---|---|---|---|---|
| | | | | | | | | | (BG1) | | (B92) | |
| | $IC_{50}{}^a$ | $R^b$ | $MIC_{80}{}^c$ | $R^b$ | $MIC_{80}{}^c$ | $R^b$ | $MIC_{80}{}^c$ | $R^b$ | $MIC_{80}{}^c$ | $R^b$ | $MIC_{80}{}^c$ | $R^b$ |
| Racemic Itraconazole$^d$ | 93 (76,115.3) | 1 | 0.5 | 1 | 0.0156 | 1 | 0.0625 | 1 | 0.5 | 1 | 0.5 | 1 |
| 23a (2S,4R,2'S) | 74 (62,115) | 0.8 | 2 | 4 | 0.0312 | 2 | 0.125 | 2 | 0.5 | 1 | 0.5 | 1 |
| 23b (2S,4R,2'R) | 106 (82,138) | 1.1 | 1 | 2 | 0.0156 | 1 | 0.25 | 4 | 0.5 | 1 | 0.5 | 1 |
| 23c (2R,4S,2'S) | 147 (123,177) | 1.6 | 2 | 4 | 0.0312 | 2 | 0.125 | 2 | 0.5 | 1 | 0.5 | 1 |
| 23d (2R,4S,2'R) | 236 (183,305) | 2.5 | 1 | 2 | 0.0312 | 2 | 0.25 | 4 | 0.5 | 1 | 0.5 | 1 |
| 23e (2S,4S,2'S) | 289 (212,393) | 3.1 | 1 | 2 | 0.0312 | 2 | 4 | 64 | 1 | 2 | 1 | 2 |
| 23f (2S,4S,2'R) | 361 (181,719) | 3.9 | 1 | 2 | 0.0156 | 1 | 4 | 64 | 0.5 | 1 | 0.5 | 1 |
| 23g (2R,4R,2'S) | 301 (173,525) | 3.2 | >4 | >8 | 0.5 | 32 | 1 | 16 | >4 | >8 | >4 | >8 |
| 23h (2R,4R,2'R) | 346 (236,508) | 3.7 | >4 | >8 | 0.5 | 32 | 2 | 32 | >4 | >8 | >4 | >8 |

$^a$nM(95% CI);

$^b$Ratios of $IC_{50}$ or MIC80 of Stereoisomer/Racemic Mixture;

$^c$µg/mL;

$^d$Mixture of the four cis-diastereomers, from Sigma-Aldrich.

FIG. 7

CHIRALLY PURE ISOMERS OF ITRACONAZOLE FOR USE AS ANGIOGENESIS INHIBITORS

CROSS REFERENCE TO RELATED APPLICATION(S)

This application is a continuation-in-part of U.S. Ser. No. 12/594,777, filed on May 2, 2011, now pending, which is a 35 U.S.C. §371 National Stage Application of PCT Application No. PCT/US08/04513 filed Apr. 7, 2008, now abandoned; which claims the benefit under 35 U.S.C. §119(e) to U.S. Application Ser. No. 60/922,059, filed Apr. 5, 2007, now abandoned; and claims the benefit of priority under 35 U.S.C. §119(e) of U.S. Ser. No. 61/474,052 filed Apr. 11, 2011. The disclosure of each of the prior applications is considered part of, and is incorporated by reference in, the disclosure of this application.

BACKGROUND OF THE INVENTION

1. Field of the Invention

The invention relates generally to angiogenesis and, more specifically, to compounds and compositions for the treatment of disorders associated with angiogenesis.

2. Background Information

Angiogenesis may be defined as the development of a blood supply to a given area of tissue. The development of a blood supply may be part of normal embryonic development, represent the revascularization of a wound bed, or involve the stimulation of vessel growth by inflammatory or malignant cells. Sometimes angiogenesis is defined as the proliferation of new capillaries from pre-existing blood vessels. New growth of soft tissue requires new vascularization, and the concept of angiogenesis is a key component of tissue growth and in particular, a key point of intervention in pathological tissue growth.

Angiogenesis is a fundamental process necessary for embryonic development, subsequent growth, and tissue repair. Angiogenesis is a prerequisite for the development and differentiation of the vascular tree, as well as for a wide variety of fundamental physiological processes including embryogenesis, somatic growth, tissue and organ repair and regeneration, cyclical growth of the corpus luteum and endometrium, and development and differentiation of the nervous system. In the female reproductive system, angiogenesis occurs in the follicle during its development, in the corpus luteum following ovulation and in the placenta to establish and maintain pregnancy. Angiogenesis additionally occurs as part of the body's repair processes, e.g., in the healing of wounds and fractures.

Nevertheless, angiogenesis is implicated in a number of important human diseases including cancer, diabetic retinopathy, and rheumatoid arthritis. Since the angiogenesis hypothesis was first put forward in 1971, the physiologic and pathological roles of angiogenesis in various biological and disease processes have been subject to extensive scrutiny. The importance of angiogenesis in human diseases such as cancer is well established. Significant progress in anti-angiogenic drug discovery and development has also been made, culminating in the development of angiogenesis inhibitors as drugs for the treatment of cancer and age-related macular degeneration. Angiogenesis inhibitors have been found to be particularly useful when used in conjunction with other chemotherapeutic drugs. Angiogenesis also contributes to the pathogenesis of a number of other diseases, including obesity, psoriasis, Kaposi's sarcoma, diabetic retinopathy, pulmonary hypertension, and arthritis. It is thus not surprising that an estimated 500 million people worldwide may benefit from treatments that modulate angiogenesis.

A number of existing drugs have been found to possess anti-angiogenic effects either serendipitously or by rational prediction. One of the first anti-angiogenic drug candidates to enter clinical trials is TNP-470, a derivative of the anti-amebic drug fumagillin, which was discovered in the late 1980s from a fungal contamination that inhibited endothelial cell culture growth. Other existing drugs such as thalidomide, non-steroidal anti-inflammatory agents and rapamycin also inhibit angiogenesis and have shown promise in clinical trials for the treatment of cancer. Although new uses for several dozen existing drugs such as fumagillin have been found serendipitously or through knowledge of pharmaceutical side effects, a systematic assembly and screening of libraries of existing drugs for novel pharmacological activities did not begin until recently. Consequently, there is a need for new specific targets which can be indicative for angiogenesis inhibition. It is therefore an object of the invention to provide a target for biological screening of compounds for angiogenesis inhibition.

Furthermore, many materials which appear promising in vitro have proven to be relatively ineffective when applied in vivo. Similarly, various of such materials have been found to be unstable, toxic, or otherwise difficult to employ. Consequently, there is a need for methods and materials capable of controlling and inhibiting angiogenesis in a reliable manner. It is therefore an object of the invention to provide compounds and pharmaceutical compositions which exhibit activity as inhibitors of angiogenesis.

SUMMARY OF THE INVENTION

The present invention is based on the seminal discovery that the stereochemistry at one end of itraconazole appears to have an influence on its biological activity. The anti-fungal activity of itraconazole is influenced by stereochemistry with trans stereoisomers demonstrating potency on the same order of magnitude as cis stereoisomers.

In one aspect, the invention provides a method for identifying a compound useful for the inhibition of angiogenesis or the treatment of a disease or disorder associated with angiogenesis, comprising the step of determining the lanosterol 14α-demethylase inhibitory activity of said compound.

In another aspect, the invention provides a method of inhibiting angiogenesis in a subject, the method comprising the step of administering to the subject an effective amount of an inhibitor of lanosterol 14α-demethylase.

In another aspect, the invention provides a method of inhibiting angiogenesis in a subject, the method comprising the step of administering to the subject an effective amount of chirally pure 4S-cis-itraconazole or a chirally pure compound of structural Formulas A-H:

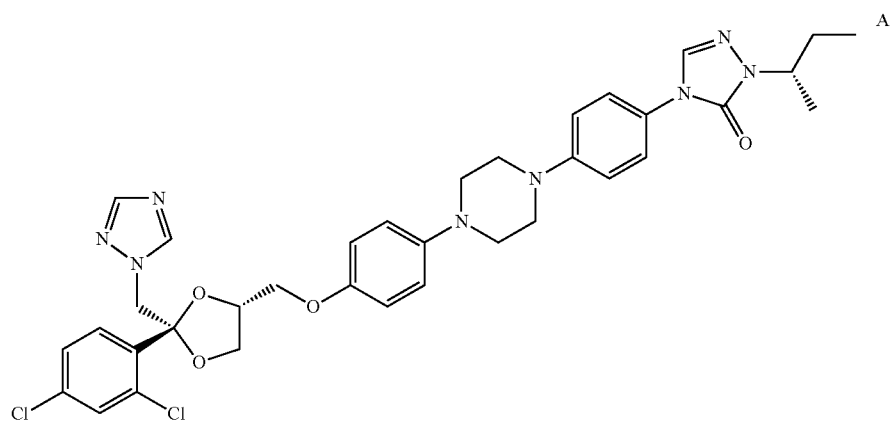
A
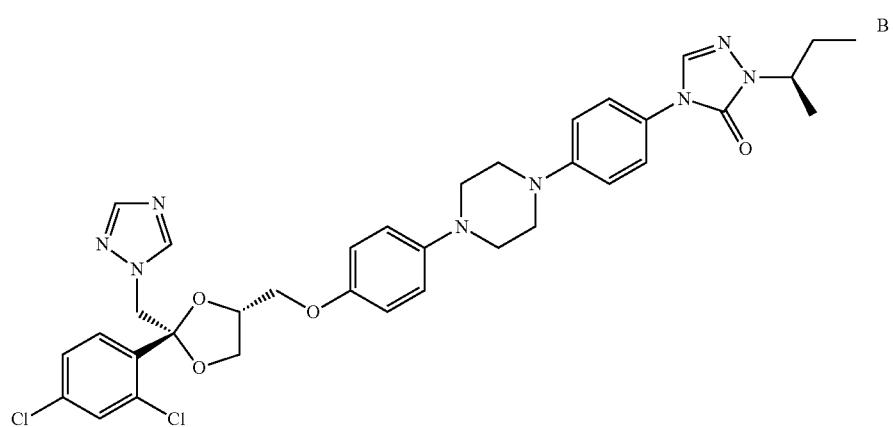
B
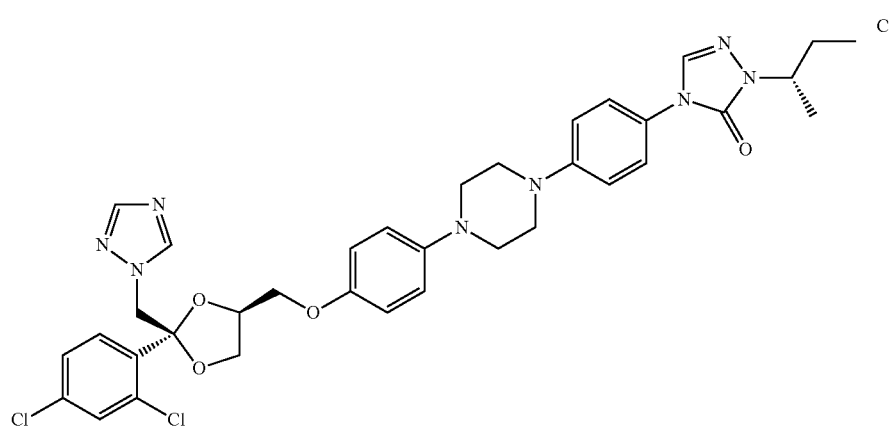
C
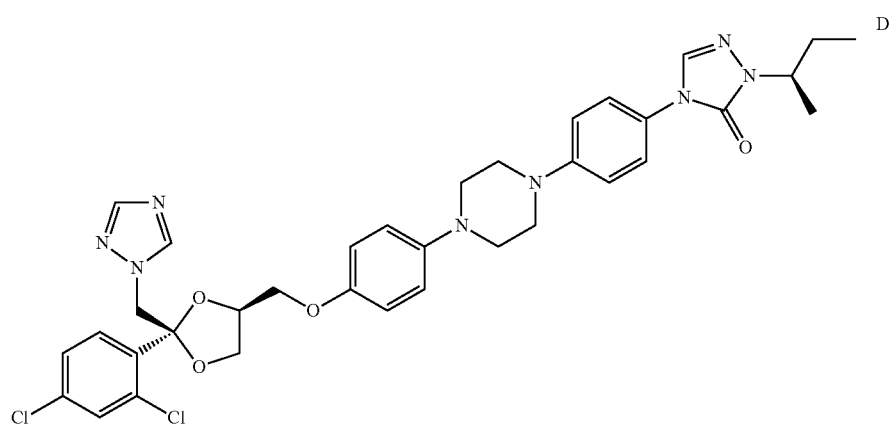
D

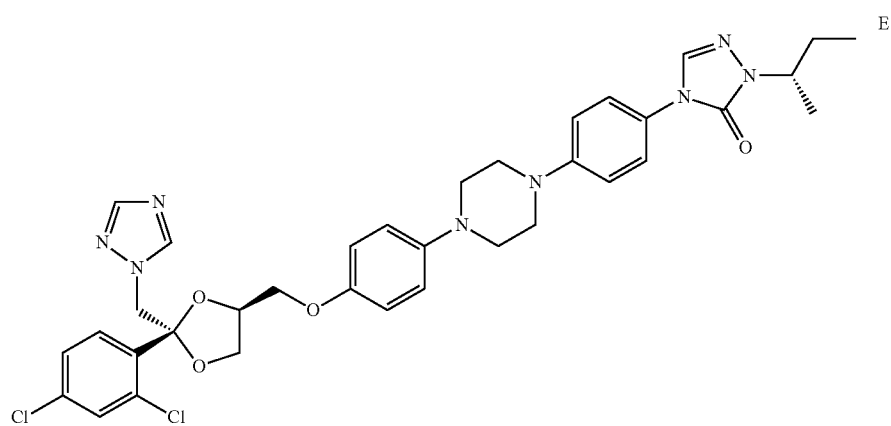
E
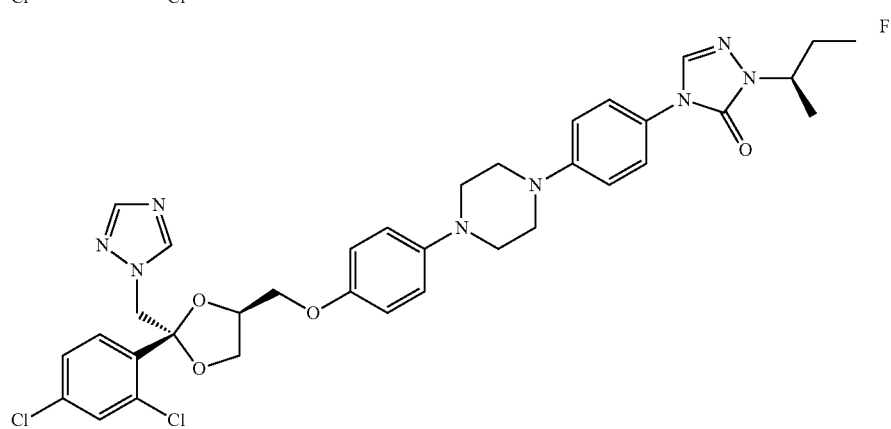
F
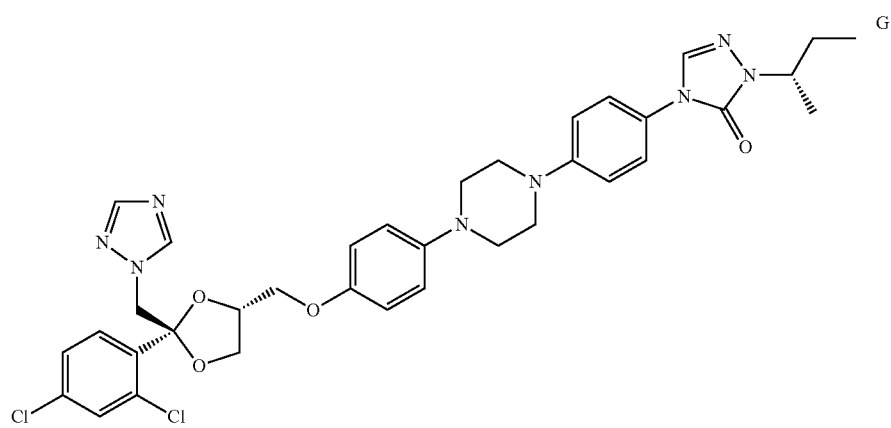
G
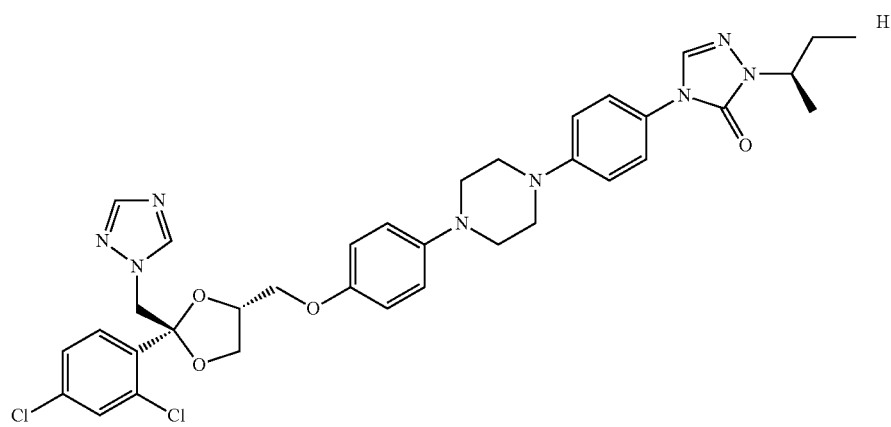
H

In another aspect, the invention provides a method of inhibiting angiogenesis in a subject, the method comprising the step of administering to the subject an effective amount of chirally pure 4R-cis-itraconazole or a chirally pure compound of structural Formulas A-H. In certain aspects, the compound administered is a chirally pure compound of structural Formulas A or B. In other aspects, the compound administered is a chirally pure compound of structural Formulas C or D.

In another aspect, the invention provides a method of inhibiting angiogenesis in a subject, the method comprising the step of administering to the subject an effective amount of azalanstat.

In another aspect, the invention provides the use of an anti-angiogenic compound in the manufacture of a medicament for inhibiting or reducing angiogenesis in a patient, where the anti-angiogenic compound is, for example, chirally pure 4S-cis-itraconazole, chirally pure 4R-cis-itraconazole, azalanstat, an inhibitor of lanosterol 14α-demethylase, or a chirally pure compound of structural Formulas A-H.

In yet another aspect, the invention provides a sustained release device for implantation in a patient and sustained release of an anti-angiogenic compound for at least a period of 30 days, wherein the anti-angiogenic compound is, for example, chirally pure 4S-cis-itraconazole, chirally pure 4R-cis-itraconazole, azalanstat, an inhibitor of lanosterol 14α-demethylase, or a chirally pure compound of structural Formulas A-H.

In yet another aspect, the invention provides a sustained release drug device adapted for implantation in or adjacent to the eye of a patient, the drug delivery device comprising: (i) a drug core comprising anti-angiogenic compound being: chirally pure 4S-cis-itraconazole, chirally pure 4R-cis-itraconazole, azalanstat, an inhibitor of lanosterol 14α-demethylase, or a chirally pure compound of structural Formulas A-H; (ii) an impermeable coating disposed about the core that is substantially impermeable to the passage of the anti-angiogenic compound, having one or more openings therein which permit diffusion of the anti-angiogenic compound, and which is substantially insoluble and inert in body fluids and compatible with body tissues; and, optionally, (iii) one or more permeable polymer members or coatings disposed in the flow path of the anti-angiogenic compound through said openings in said impermeable coating, said permeable polymer being permeable to the passage of the anti-angiogenic compound, and which is substantially insoluble and inert in body fluids and compatible with body tissues; wherein the impermeable coating and permeable polymer members or coatings are disposed about the drug core so as to produce, when implanted, a substantially constant rate of release of the anti-angiogenic compound from the device.

In another aspect, the invention provides a sustained release formulation for depot injection in a patient and sustained release of an anti-angiogenic compound for at least a period of 30 days, wherein the formulation includes:

a viscous gel formulation comprising a bioerodible, biocompatible, polymer; and an anti-angiogenic agent dissolved or dispersed therein, which anti-angiogenic agent is: chirally pure 4S-cis-itraconazole, chirally pure 4R-cis-itraconazole, azalanstat, an inhibitor of lanosterol 14α-demethylase, or a chirally pure compound of structural Formulas A-H.

In one embodiment, the invention provides a method, use, device, or formulation, wherein the anti-angiogenic compound is provided in an amount effective for treatment of retinoblastoma, cystoid macular edema (CME), exudative age-related macular degeneration (AMD), diabetic retinopathy, diabetic macular edema, or ocular inflammatory disorders.

In another embodiment, the invention provides a method, use, device, or formulation for treatment of a tumor.

In another embodiment, the invention provides a method, use, device, or formulation for the treatment of dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

In yet another embodiment, the invention provides a method, use, device, or formulation for eliminating or reducing normal but undesired tissue in a patient.

In still another embodiment, the invention provides a method, use, device, or formulation for the reduction of fat.

In a certain embodiment, the invention provides a method, use, device or formulation, wherein the anti-angiogenic compound inhibits endothelial cell proliferation.

In a certain embodiment, the invention provides a method, use, device or formulation, wherein the anti-angiogenic compound inhibits G1/S cell cycle progression of endothelial cells.

In a certain embodiment, the invention provides a method, use, device or formulation, wherein the anti-angiogenic compound decreases new blood vessel formation.

In another embodiment, the invention provides a method, use, device or formulation, further comprising an additional therapeutic agent.

In a certain embodiment, the invention provides a method, use, device or formulation, wherein the additional therapeutic agent is an angiogenesis-inhibiting compound. In a certain embodiment, the invention provides a method, use, device or formulation, wherein the additional therapeutic agent is an anticancer compound.

In a certain embodiment, the invention provides a method, use, device or formulation, wherein the step of administering the anti-angiogenic compound comprises administering the compound orally, topically, parentally, intravenously or intramuscularly.

In a certain embodiment, the invention provides a method, use, device or formulation, wherein the administration is carried out in a controlled and sustained release.

In a certain embodiment, the invention provides a method, use, device or formulation, wherein the step of administering the anti-angiogenic compound comprises administering the compound in a dosage of between about 0.1 and 100 mg/kg/day.

In a certain embodiment, the invention provides a method, use, device or formulation, wherein the step of administering the anti-angiogenic compound comprises administering the compound in a dosage of less than about 500 mg/day.

In a certain embodiment, the invention provides a method, use, device or formulation, wherein the subject is a human.

In another aspect, the invention provides a kit comprising an effective amount of an anti-angiogenic compound in unit dosage form, together with instructions for administering the anti-angiogenic compound to a subject suffering from or susceptible to a disease or disorder or symptoms thereof associated with angiogenesis.

In a certain embodiment, the invention provides a method, use, device or formulation, comprising the step of administering an effective amount of a composition comprising an anti-angiogenic compound and a pharmaceutically suitable excipient.

In a certain embodiment, the invention provides a method, use, device or formulation of any of the preceding claims, wherein the disease or disorder associated with angiogenesis is selected from: tumor or cancer growth (neoplasia), skin disorders, neovascularization, and inflammatory and arthritic diseases. In a certain embodiment, the disease or disorder associated with angiogenesis is tumor or cancer growth (neoplasia). In a certain embodiment, the disease or disorder is: eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In a certain embodiment, the disease or disorder associated with angiogenesis is a skin disorder. In a certain embodiment, the disease or disorder is: psoriasis, acne, rosacea, warts, eczema, hemangiomas, lymphangiogenesis, Sturge-Weber syndrome, venous ulcers of the skin, neurofibromatosis, and tuberous sclerosis.

In a certain embodiment, the disease or disorder associated with angiogenesis is neovascularization. In certain embodiments, the disease or disorder is: diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle). In a certain embodiment, the disease or disorder associated with angiogenesis is rheumatoid arthritis, diabetic retinopathy, macular edema, or macular degeneration.

In a certain embodiment, the disease or disorder associated with angiogenesis is inflammatory and arthritic disease. In a certain embodiment, the disease or disorder is: rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In certain embodiments, the subject anti-angiogenic compounds are used as part of a treatment or prevention for an optic neuropathy. The compounds can be administered, for example, by for intraocular injection or implantation. The anti-angiogenic compound can be administered alone, or in combination with other agents, including anti-inflammatory compounds, neuroprotective agents, agents that reduce introcular pressure (TOP), and/or immunomodulatory compounds. For instance, the anti-angiogenic compound can be administered as part of therapy that includes treatment with a cholinergic agonists, cholinesterase inhibitors, carbonic anhydrase inhibitors, adrenergic agonists (such as alpha2-selective adrenergic agonists), beta-blockers, prostaglandin analogues, osmotic diuretics, p38 kinase antagonists, Cox-2 inhibitors, corticosteroid (such as triamcinolone, dexamethasone, fluocinolone, cortisone, prednisolone, flumetholone, or derivatives thereof such as triamcinolone acetonide or fluocinolone acetonide), salts thereof, isomers thereof, prodrugs thereof, and mixtures of any of these.

As used herein, the terms "optic neuropathy", or "optic neuropathies" are intended to include diseases, disorders, or damage to the nerves or other structures of the eye. By way of example, such optic neuropathies include uveitis, such as anterior uveitis, intermediate uveitis, posterior uveitis, and diffuse uveitis; uveitic syndromes, such as ankylosing spondylitis, juvenile rheumatoid arthritis, pars planitis, toxoplasmosis, cytomegalovirus, inflammation caused by herpes zoster, inflammation caused by herpes simplex, toxocariasis, birdshot chorioretinopathy, presumed ocular histoplasmosis syndrome, syphilis, tuberculosis, Vogt-Koyanagi-Harada syndrome, sympathetic ophthalmia, ocular sarcoidosis and endophthalmitis; masquerade syndromes, such as intraocular malignancy, retinitis pigmentosa, and reactions to drugs; vascular retinopathies, such as hypertensive retinopathy, diabetic retinopathy, central retinal artery occlusion, and central retinal vein occlusion; age-related macular degeneration; retinitis pigmentosa; glaucoma; ocular hypertension; optic nerve and pathway disorders, such as papilledema, papillitis, retrobulbar neuritis, toxic amblyopia, optic atrophy, bitemporal hemianopia, and homonymous hemianopia. In certain preferred embodiments, the subject anti-angiogenic compounds are used as part of a treatment for uveitis, Diabetic Macular Edema (DME), Wet ARMD, and CMV retinitis.

There are various sustained release drug delivery devices for implantation in the eye and treating various eye diseases that can be readily adapted for delivery of the subject anti-angiogenic compounds. Examples are found in the following patents, the disclosures of which are incorporated herein by reference: U.S. 2005/0137583 (Renner); U.S. 2004/0219181 (Viscasillas); U.S. 2004/0265356 (Mosack); U.S. 2005/0031669 (Shafiee); U.S. 2005/0137538 (Kunzler); U.S. 2002/0086051A1 (Viscasillas); U.S. 2002/0106395A1 (Brubaker); U.S. 2002/0110591A1 (Brubaker et al.); U.S. 2002/0110592A1 (Brubaker et al.); U.S. 2002/0110635A1 (Brubaker et al.); U.S. Pat. No. 5,378,475 (Smith et al.); U.S. Pat. No. 5,773,019 (Ashton et al.); U.S. Pat. No. 5,902,598 (Chen et al.); U.S. Pat. No. 6,001,386 (Ashton et al.); U.S. Pat. No. 6,726,918 (Wong); U.S. Pat. No. 6,331,313 (Wong); U.S. Pat. No. 5,824,072 (Wong); U.S. Pat. No. 5,632,984 (Wong); U.S. Pat. No. 6,217,895 (Guo et al.); U.S. Pat. No. 6,375,972 (Guo et al.). In certain embodiments, the device include an inner drug core including the anti-angiogenic compound, and some type of holder for the drug core made of an impermeable material such as silicone or other hydrophobic materials. The holder includes one or more openings for passage of the pharmaceutically agent through the impermeable material to eye tissue. Many of these devices include at least one layer of material permeable to the active agent, such as polyvinyl alcohol.

In still another embodiment, the invention provides a process for preparing of 4R-cis-itraconazole or 4S-cis-itraconazole comprising the step of:

reacting the a compound of the formula:

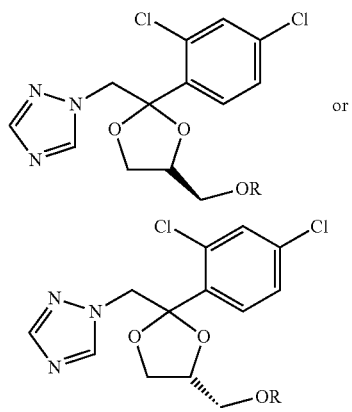

wherein R is a protecting group with a compound of the formula:

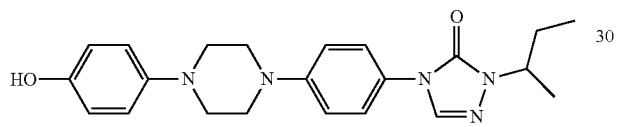

in the presence of base. In this process, the compound of the formula:

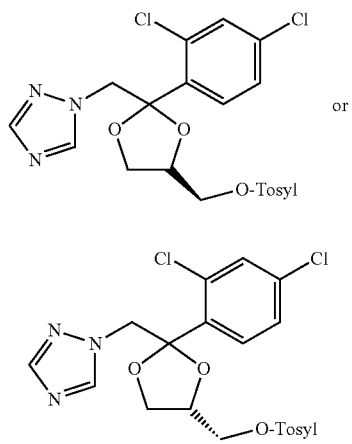

may be prepared by reacting a compound of the formula with a compound of the formula

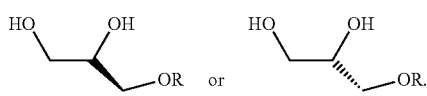

The individual stereoisomers of formulas

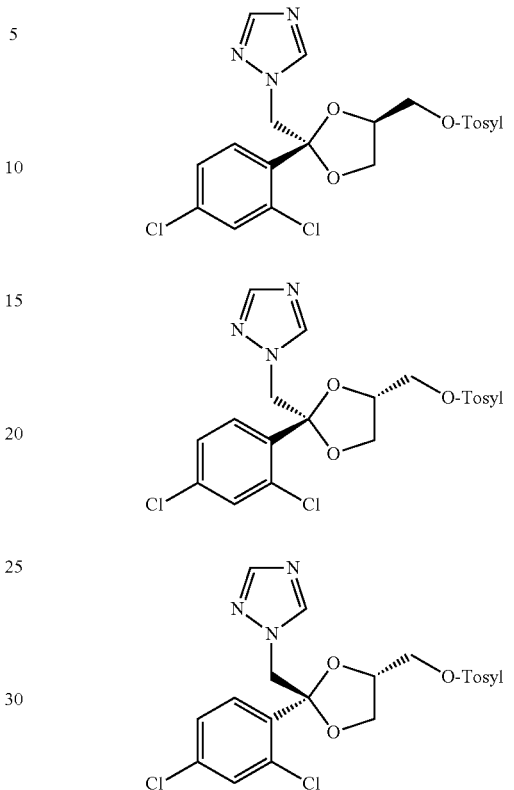

may be obtained by separation techniques known in the art including, but not limited to, chromatography, HPLC, crystallization, recrystallization, double-recrystallization, and so on.

In other embodiments, processes for preparing compounds of structural Formulas A-H are provided. Compounds of structural Formulas A (4-(4-(4-(4-(((2S,4R)-2-((1H-1,2,4-triazol-1-yl)methyl)-2-(2,4-dichlorophenyl)-1,3-dioxolan-4-yl)methoxy)phenyl)piperazin-1-yl)phenyl)-1-((S)-sec-butyl)-1H-1,2,4-triazol-5(4H)-one) or B (4-(4-(4-(4-(((2S,4R)-2-((1H-1,2,4-triazol-1-yl)methyl)-2-(2,4-dichlorophenyl)-1,3-dioxolan-4-yl)methoxy)phenyl)piperazin-1-yl)phenyl)-1-((R)-sec-butyl)-1H-1,2,4-triazol-5(4H)-one), may be prepared by:

reacting a compound of structural Formula I with (S)- or (R)-1-(sec-butyl)-4-(4-(4-(4-hydroxyphenyl)piperazin-1-yl)phenyl)-1H-1,2,4-triazol-5(4H)-one, respectively in the presence of a base:

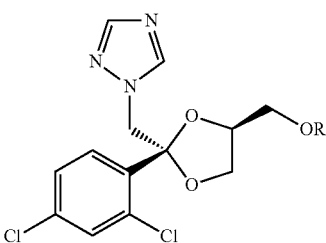

I

Compounds of structural Formula C (4-(4-(4-(4-(((2R,4S)-2-((1H-1,2,4-triazol-1-yl)methyl)-2-(2,4-dichlorophenyl)-1,3-dioxolan-4-yl)methoxy)phenyl)piperazin-1-yl)phenyl)-1-((S)-sec-butyl)-1H-1,2,4-triazol-5(4H)-one) or D (4-(4-(4-(4-(((2R,4S)-2-((1H-1,2,4-triazol-1-yl)methyl)-2-(2,4-dichlorophenyl)-1,3-dioxolan-4-yl)methoxy)phenyl)piperazin-1-yl)phenyl)-1-((R)-sec-butyl)-1H-1,2,4-triazol-5(4H)-one), may be prepared by:

reacting a compound of structural Formula II with (S)- or (R)-1-(sec-butyl)-4-(4-(4-(4-hydroxyphenyl)piperazin-1-yl)phenyl)-1H-1,2,4-triazol-5(4H)-one, respectively in the presence of a base:

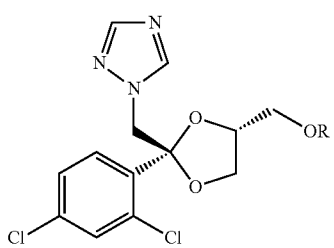

II

Compounds of structural Formula E (4-(4-(4-(4-(((2S,4S)-2-((1H-1,2,4-triazol-1-yl)methyl)-2-(2,4-dichlorophenyl)-1,3-dioxolan-4-yl)methoxy)phenyl)piperazin-1-yl)phenyl)-1-((S)-sec-butyl)-1H-1,2,4-triazol-5(4H)-one) or F (4-(4-(4-(4-(((2S,4S)-2-((1H-1,2,4-triazol-1-yl)methyl)-2-(2,4-dichlorophenyl)-1,3-dioxolan-4-yl)methoxy)phenyl)piperazin-1-yl)phenyl)-1-((R)-sec-butyl)-1H-1,2,4-triazol-5(4H)-one), may be prepared by:

reacting a compound of structural Formula III with (S)- or (R)-1-(sec-butyl)-4-(4-(4-(4-hydroxyphenyl)piperazin-1-yl)phenyl)-1H-1,2,4-triazol-5(4H)-one, respectively in the presence of a base:

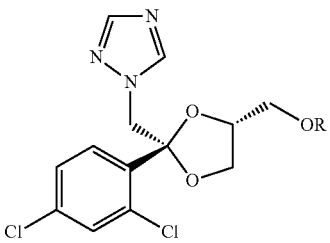

III

Compounds of structural formula G (4-(4-(4-(4-(((2R,4R)-2-((1H-1,2,4-triazol-1-yl)methyl)-2-(2,4-dichlorophenyl)-1,3-dioxolan-4-yl)methoxy)phenyl)piperazin-1-yl)phenyl)-1-((S)-sec-butyl)-1H-1,2,4-triazol-5(4H)-one) or H (4-(4-(4-(4-(((2R,4R)-2-((1H-1,2,4-triazol-1-yl)methyl)-2-(2,4-dichlorophenyl)-1,3-dioxolan-4-yl)methoxy)phenyl)piperazin-1-yl)phenyl)-1-((R)-sec-butyl)-1H-1,2,4-triazol-5(4H)-one), may be prepared by:

reacting a compound of structural Formula IV with (S)- or (R)-1-(sec-butyl)-4-(4-(4-(4-hydroxyphenyl)piperazin-1-yl)phenyl)-1H-1,2,4-triazol-5(4H)-one, respectively in the presence of a base:

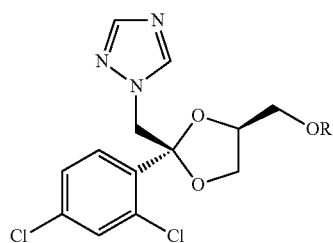

IV

In certain aspects, R is a suitable leaving group, such as a tosylate ester, sulfate ester, nitrate ester, phosphate ester, carboxylate ester, and the like.

Similarly, the compound of the formula:

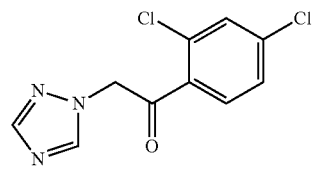 [SMILES: O=C(Cn1cncn1)c1ccc(Cl)cc1Cl]

may be prepared by reacting 1,2,4 triazole with a compound of the formula in the

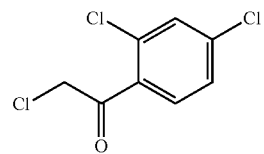 [SMILES: O=C(CCl)c1ccc(Cl)cc1Cl]

presence of base.

Also, the compound of the formula:

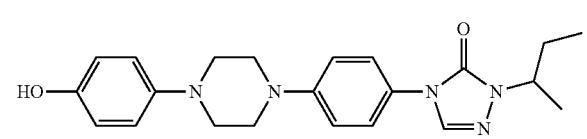 [SMILES: CCC(C)n1ncn(-c2ccc(N3CCN(c4ccc(O)cc4)CC3)cc2)c1=O]

may be prepared by a process, comprising:
a.) reacting a compound for the formula:

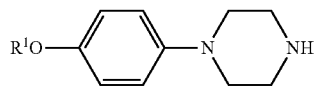

wherein $R^1$ is an alkyl protecting group
with para-chloro-nitrobenzene to form a compound of the formula:

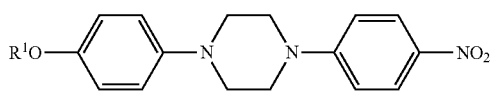

b.) hydrogenating the product of a.);
c.) reacting the hydrogenation product of b.) with phenylchloroformate to form a compound of the formula:

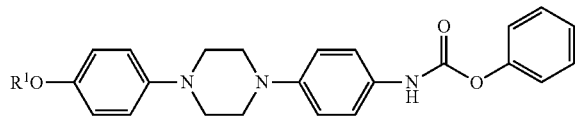

d.) reacting the product of c.) with N'-sec-butylformohydrazine to form a compound of the formula:

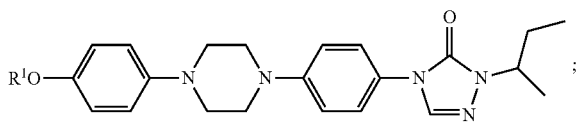

and
e.) deprotecting the product of d.).
Other aspects of the invention are disclosed infra.

BRIEF DESCRIPTION OF THE DRAWINGS

FIG. 1 shows the inhibition endothelial cell proliferation and blocks in vivo angiogenesis by itraconazole. (a) Screening results for 2,604 existing drugs on HUVEC proliferation at 10 μM. (b) Inhibition of HUVEC (●) and human foreskin fibroblast (○) proliferation by itraconazole. (c) Cell cycle analysis of HUVEC showing G1/S arrest upon 4S-cis itraconazole treatment.

FIG. 5 is a table that provides the chiral HPLC analysis data (retention time) and optical rotation measurements of the eight itraconazole stereoisomers.

FIG. 6 is a table that provides the high-resolution mass spectrometry data for the eight itraconazole stereoisomers.

FIG. 7 is a table showing the potency of each of the eight isolated itraconazole stereoisomers in snit-fungal and HUVEC biological assays.

DETAILED DESCRIPTION OF THE INVENTION

Figure 2A:
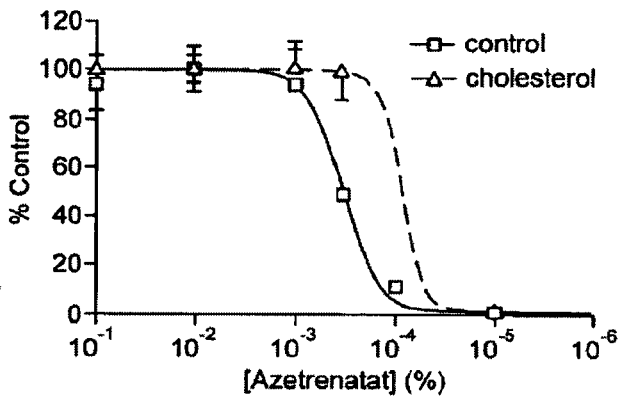
FIG. 2 shows the effect of cholesterol on the inhibition of BAEC proliferation by itraconazole and azalanstat. BAEC were incubated in DMEM, 10% lipoprotein deficient serum (LPDS) with indicated concentrations of itraconazole (a) azalanstat (b) or TNP-470 (c) either alone or in combination with 40 μg/ml free cholesterol for 36 h. Cells were then pulsed with 1 μCi [$^3$H]-thymidine for 8 h before they are harvested for scintillation counting.

Itraconazole, used clinically as an antifungal agent, potently inhibits in vitro proliferation of human umbilical vein endothelial cells (HUVEC) and angiogenesis in vivo. The target responsible for itraconazole's antifungal activity is lanosterol 14α-demethylase (14DM), a key enzyme involved in the biosynthesis of ergosterol, which is required for the integrity of the fungal cell membrane. However, the role of human 14DM in the inhibition of angiogenesis by itraconazole remains unclear. The poor correlation between human 14DM inhibition and antiangiogenic activity for several structurally related potent azole antifungal drugs implies that other primary molecular target(s) might be responsible for the antiangiogenic activity of itraconazole with 14DM making only a partial contribution.

Itraconazole contains three stereocenters, which can yield a total of eight stereoisomers. The dioxolane ring harbors two chiral centers, while the third one marked as 2' resides on the sec-butyl side chain appended to the triazolone ring (Scheme 2).

As an anti-fungal drug, the pill and i.v. formulations of itraconazole are supplied as a 1:1:1:1 mixture of four cis-stereoisomers. Although the antifungal activity and metabolism of individual cis stereoisomers of itraconazole have been reported, the activity of the trans-stereoisomers, 23e-23h, have not been disclosed to date. Furthermore, itraconazole has not been examined for antiangiogenic activity in any of its stereochemically pure forms. Previous efforts have been limited to the synthesis and determination of the antiangiogenic activity of the epimeric mixtures of 4R- and 4S-cis itraconazole. Thus, the complete role of stereochemistry in the two activities of itraconazole has not been addressed.

The present disclosure is based in part on the discovery that isolated stereoisomers are significantly more effective in the inhibition of growth of endothelial cells. In addition, this increase in therapeutic effectiveness may allow for the use of significantly lower doses, depending on the patient, the condition or infection treated and the route of administration. The anti-fungal activity of the trans-stereoisomers and the antiangiogenic activity of the eight stereochemically pure forms of itraconazole are described herein. Furthermore, the role of human 14α-demethylase (14DM) in the inhibition of angiogenesis by itraconazole is provided.

To systematically explore the effect of absolute stereochemistry at every chiral center of itraconazole on both antifungal and antiangiogenic activity, all the eight stereoisomers were synthesized and a comparison of their respective antiangiogenic and antifungal activities was made. As disclosed herein, all eight stereoisomers of itraconazole (23a-23h) have been synthesized and evaluated for activity against human endothelial cell proliferation and for antifungal activity against five fungal strains.

The total synthesis of 4S-cis-itraconazole and 4R-cis-itraconazole is shown in Scheme 1.

Scheme 1
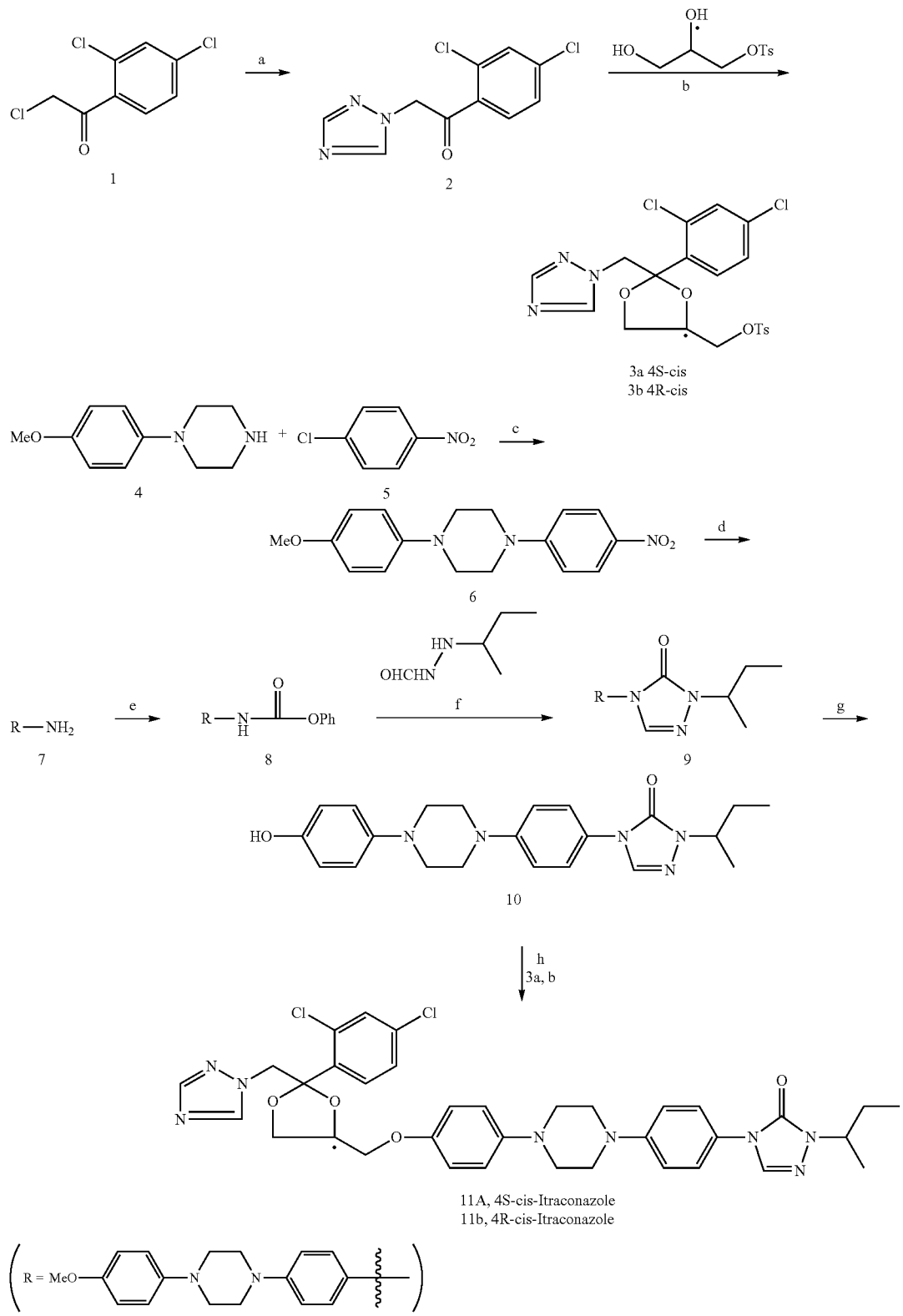
In Scheme 1, a diastereoselective ketalization of intermediate compound 2 using a chirally pure glycerol monotosylate afforded the chirally pure intermediates 3a and 3b.
Similarly, another intermediate, 10, was synthesized via a five-step sequence starting from the piperazine precursor 4 and 4-chloronitrobenzene 5. The final coupling of tosylate 3a or 3b and phenol 10 was carried out under basic conditions to give pure 4S-cis-itraconazole or 4R-cis-itraconazole in good yield.

The inhibitory activity of these diasteromers was then determined using a HUVEC proliferation assay. The 4R-cis diastereomer ($IC_{50}=0.056\pm0.01$ μM) was found to be about 20-fold more potent than the 4S-cis stereoisomer ($IC_{50}=1.1\pm0.13$ μM). In comparison, the racemic itraconazole has an $IC_{50}$ of 0.16 μM.

To systematically explore the effect of absolute stereochemistry at every chiral center of itraconazole on both antifungal and antiangiogenic activity, all eight stereoisomers were synthesized and their antiangiogenic and antifungal activities compared.

into the triazolone via the phenylcarbamate and semicarbazide intermediates. The stereochemistry at 2' position in 23a-23h was inherited from the optically pure starting material, (R)-(−)-2-butanol (17a) or (S)-(+)-2-butanol (17b). In order to achieve a stereospecific N-alkylation of triazolone 12 by tosylate displacement of 18a or 18b, the proton abstraction of triazolone nitrogen was conducted using potassium carbonate in conjunction with 18-crown-6 in order to enhance the nucleophilicity of the nitrogen anion by forming loose ion-pairs. Construction of the 1,3-dioxolane ring in 22a-22d was achieved by acid-assisted ketalization of 2,2',4'-trichloroacetophenone 2 with optically pure glyceryl tosylate 21a or 21b. While the stereochemistry at C-4 in 22a-22d emanates from the chiral starting material 21a or 21b, C-2, the new chiral

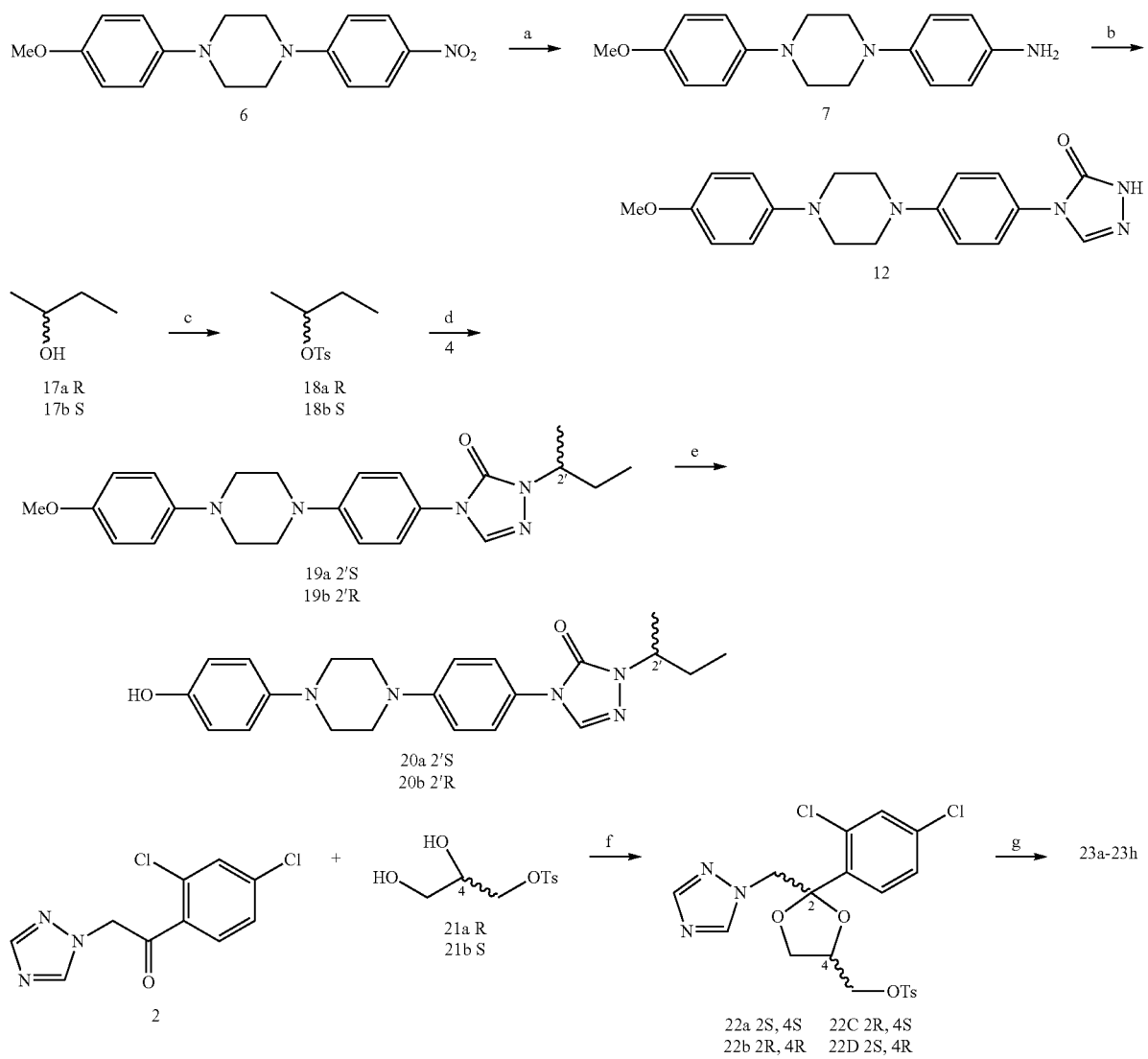

Scheme 2

The total synthesis began by reduction of the nitro group in N-(4-methoxyphenyl)-N-(4-nitrophenyl)-piperazine 6 (Scheme 2) using a palladium-catalyzed transfer hydrogenation. The use of hydrazine as a hydrogen source produced much higher yields of aniline 7 compared with ammonium formate. The amino group in 7 was subsequently transformed center, is generated during ketalization. The ratio of cis- versus trans-diastereomers 22a/22c or 22b/22d is dictated by the steric effects, and a preponderance of cis-dioxolane is typically afforded. The cis-diastereomer (22a or 22b) was separated from the trans-diastereomer (22c or 22d) and further purified by double-recrystallization.

The significant influence of stereochemistry at one end of itraconazole on its activity suggests that this part of itraconazole may participate in a stereospecific interaction with target(s) in endothelial cells. Thus in some aspects, the invention provides the use of chirally pure 4S-cis-itraconazole. Nevertheless, in other embodiments, the invention provides the use of chirally pure 4R-cis-itraconazole. As used herein, the term "chirally pure" means substantially free of any other stereoisomer. For a compound to be substantially free of any other stereoisomer means that the compound is made up of a significantly greater proportion of the indicated stereoisomer than of its optical antipode (in the case of optical isomers), or any other diastereomer (resulting when a compound has more than one stereocenter). In some aspects of the invention, for a compound to be substantially free of any other stereoisomer means that the compound is made up of at least about 90% by weight of the indicated stereoisomer and about 10% by weight or less of any other stereoisomer. In still other aspects of the invention, for a compound to be substantially free of any other stereoisomer means that the compound is made up of at least about 95% by weight of the indicated stereoisomer and about 5% by weight or less of any other stereoisomer. In yet other aspects of the invention, for a compound to be substantially free of any other stereoisomer means that the compound is made up of at least about 99% by weight of the indicated stereoisomer and about 1% by weight or less of any other stereoisomer. In another aspect of the invention, for a compound to be substantially free of any other stereoisomer means that the compound is made up of nearly 100% by weight of the indicated stereoisomer. The above percentages are based on the total amount of the combined stereoisomers of the compound.

The present invention is based on the discovery that various classes of compounds that have already been demonstrated as tolerable in human patients as part of other therapies, also have potent anti-angiogenic activities. In general, the compounds of the present invention inhibit endothelial cell proliferation. In certain preferred embodiments, the anti-angiogenic activity derives at least in part from the ability of the compound to inhibit progression through the G1/S point of the cell cycle.

In one aspect, the invention provides a method of inhibiting or otherwise reducing angiogenesis in a subject using a treatment protocol that includes administering a compound that inhibits lanosterol 14α-demethylase (14DM). As described in further detail below, it has been discovered that inhibition of 14DM in endothelial cells can prevent their proliferation, and makes 14DM inhibitors useful as anti-angiogenic agents. 14DM, catalyzes an essential step in the biosynthesis of ergosterol required for the membrane integrity of fungal cells. The demethylation of lanosterol is a common step between fungi and humans in sterol biosynthesis prior to the divergence of the pathways leading to ergosterol in fungi and cholesterol in humans, respectively. Although itraconazole as well as other azole antifungal drugs preferably inhibit the fungal 14DM over its human counterparts, they do inhibit the human enzyme at higher concentrations. The $IC_{50}$ values of itraconazole for human 14DM varies from 0.61 µM to 30 µM for unknown reasons. While not wishing to be bound by any particular theory, the inhibition of endothelial cell cycle by itraconazole may be mediated at least in part through the inhibition of human 14DM.

In the case of dioxolane-containing azole antifungals like itraconazole, ketoconazole, and terconazole, it has been noted that the cis-diastereomeric pairs exhibit much higher antifungal potency over their trans counterparts and thus for efficacy reasons they have been used clinically as mixtures of cis-diastereomers. Docking studies performed based on fluconazole-MtCYP51 (referred to as 14DM for human enzyme) crystal structure have offered an explanation to this effect. Homology-modeled CaCYP51 complexed with different stereoisomers of ketoconazole have been analyzed and it was observed that the cis-pairs (2S4R and 2R4S) and only one of the trans pairs, namely 2S4S-ketoconazole, avidly bind to CaCYP51, which is in good agreement with reported $IC_{50}$ values of the stereoisomers of ketoconazole against *C. albicans* (J. Med. Chem. 1992; 35: 2818-2825). Antifungal activities measured herein for the eight stereoisomers of itraconazole against the three ascomycetes perfectly match the pattern observed with ketoconazole. It is possible that the CYP51 enzymes of ascomycetes poorly bind the 2R4R itraconazole, whereas in the case of phylogenetically distant *C. neoformans*, this scenario of binding among the trans-pairs is quite the opposite. This may also be explained by the expression of a stereoselective efflux pump or catabolic enzyme in this strain. Taken together, these data indicate that unlike HUVEC inhibition, the sensitivity of fungal growth to itraconazole is dictated not by cis-trans configuration of the dioxolane ring but instead by the absolute stereochemistry at the 2 and 4 carbons. The only commonality that was observed for the role of stereochemistry in HUVEC and fungal inhibition was that the stereochemistry at the 2' position had little influence on potency in either case.

All the cis-diastereomers, which make up the commercial itraconazole, exhibited high potency in both HUVEC and fungal inhibition. All the trans diastereoisomers were less potent in HUVEC proliferation than were the cis diastereoisomers. In contrast, one pair of trans diastereoisomers, 23e and 23f, were roughly as potent as the cis-diastereomers with respect to antifungal activity against four out of five strains. The lack of correlation between HUVEC and fungal sensitivity to optically pure itraconazole stereoisomers suggests that human 14DM is not likely to be the major target for the antiangiogenic activity of itraconazole. There is evidence that suggests that the inhibitory effect of itraconazole on endothelial cells results largely from its inhibition of cholesterol trafficking through the lysosomal compartment, leading to inhibition of the mTOR pathway. The results disclosed herein provide previously unavailable data on the role of stereochemistry in the potency of itraconazole against an emerging therapeutic target for this drug, angiogenesis. Distinct antiangiogenic and antifungal activity profiles of the trans-stereoisomers, provided herein, especially 23e and 23f, suggest different molecular mechanisms underlying the anti-angiogenic and anti-fungal activities of itraconazole. Compounds 23a and 23b possess the greatest antiangiogenic potential and therefore are good candidates for lead compounds for further optimization of itraconazole as an antiangiogenic drug.

Thus, in one aspect, the invention provides a method of inhibiting angiogenesis in a subject, the method comprising the step of administering to the subject an angiogenesis-inhibiting compound, wherein the compound is an inhibitor of 14DM.

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is an inhibitor of 14DM.

In still another aspect, the invention provides a method of inhibiting angiogenesis in a subject, the method comprising the step of administering to the subject an angiogenesis-inhibiting compound, wherein the compound is 4S-cis-itraconazole.

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is 4S-cis-itraconazole.

In still another aspect, the invention provides a method of inhibiting angiogenesis in a subject, the method comprising the step of administering to the subject an angiogenesis-inhibiting compound, wherein the compound is 4R-cis-itraconazole.

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is 4R-cis-itraconazole.

In another aspect, the invention provides a method of inhibiting angiogenesis in a subject, the method comprising the step of administering to the subject an angiogenesis-inhibiting compound, wherein the compound is azalanstat.

In yet another aspect, the invention provides a method of treating a subject identified as suffering from or susceptible to a disease or disorder associated with angiogenesis, the method comprising the step of administering to the subject a therapeutic amount of an angiogenesis-inhibiting compound, wherein the compound is azalanstat.

In another aspect, the invention provides a method of inhibiting angiogenesis in a subject, treating a subject identified as suffering from or susceptible to a disease or disorder associated with angiogenesis, or any method delineated herein, wherein the subject is identified as to be in need of such treatment (e.g., angiogenesis reduction or inhibition).

In a certain embodiment, itraconazole inhibits angiogenesis by inhibiting endothelial cell proliferation. In another embodiment, itraconazole is a G1/S cell cycle inhibitor.

In a certain embodiment, the invention further comprises an additional therapeutic agent. In a further embodiment, the additional therapeutic agent is an angiogenesis-inhibiting compound. In another further embodiment, the additional therapeutic agent is an anticancer compound.

In a certain embodiment, the disease or disorder associated with angiogenesis is selected from: tumor or cancer growth (neoplasia), skin disorders, neovascularization, and inflammatory and arthritic diseases.

In a certain embodiment, the step of administering the angiogenesis-inhibiting compound comprises administering the compound orally, topically, parentally, intravenously or intramuscularly.

In a certain embodiment, the step of administering the angiogenesis-inhibiting compound comprises administering the compound in a dosage of between about 0.1 and 100 mg/kg/day. In another embodiment, the step of administering the angiogenesis-inhibiting compound comprises administering the compound in a dosage of less than about 500 mg/day.

In a certain embodiments, the subject is an animal or human.

In a certain embodiment, the invention provides a kit comprising an effective amount of an angiogenesis-inhibiting compound in unit dosage form, together with instructions for administering the angiogenesis-inhibiting compound to a subject suffering from or susceptible to a disease or disorder or symptoms thereof associated with angiogenesis. In a further embodiment, the angiogenesis-inhibiting compound is MPA.

In a certain embodiment, the invention provides administering an effective amount of a composition comprising an angiogenesis-inhibiting compound and a pharmaceutically suitable excipient.

This instant invention is based on the premise that there exist unappreciated physiological activities among known clinical drugs demonstrating inhibition of lanosterol 14α-demethylase. This premise was proven by the identification of multiple known drugs with unexpected inhibitory effects on endothelial cell proliferation in vitro and angiogenesis in vivo. In addition to the endothelial cell proliferation assay, a library in a number of other cellular assays was screened. It was found that the hit rates with this drug library are significantly higher than commercially available small molecule libraries on more than half a dozen cellular screens. The molecular basis of these high hit rates may lie in the shared genome and largely overlapping proteome of all human cell types and tissues. Significant redundancy exists in the usage of individual genes in different physiological as well as pathological processes. Thus, there is great potential in screening existing drugs for novel biological and therapeutic activities.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

The term "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "anti-angiogenic compound" and "angiogenesis inhibiting compound" may be used interchangeably.

The term "tumor" is used to describe an abnormal growth in tissue which occurs when cellular proliferation is more rapid than normal tissue and continues to grow after the stimuli that initiated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized.

The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor. Methods of treating tumors and/or cancer according to the present invention comprise administering to a patient in need thereof an effective amount of one or compounds according to the present invention.

Angiogenesis is used throughout the specification to describe the biological processes which result in the development of blood vessels or increase in the vascularity of tissue in an organism. Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases or disorders treated, ameliorated or prevented by the instant invention include the following: neoplasia, internal malignancies such as eye or ocular cancer, rectal cancer, colon cancer, cervical cancer, prostate cancer, breast cancer and bladder cancer, benign and malignant tumors, including various cancers such as, anal and oral cancers, stomach, rectal, liver, pancreatic, lung, cervix uteri, corpus uteri, ovary, prostate, testis, renal, mouth/pharynx, esophageal, larynx, kidney, brain/cns (e.g., gliomas), head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, lymphoma, neurofibromatosis, tuberous sclerosis (each of which conditions produces benign tumors of the skin), hemangiomas, lymphangiogenesis, rhabdomyosarcomas, retinoblastoma, osteosarcoma, acoustic neuroma, neurofibroma, trachoma, pyogenic granulomas, blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen, psoriasis, acne, rosacea, warts, eczema, neurofibromatosis, Sturge-Weber syndrome, venous ulcers of the skin, tuberous sclerosis, chronic inflammatory disease, arthritis, lupus, scleroderma, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium, keratitis sicca, Sjogren's, phylectenulosis, syphilis, *Mycobacteria* infections, lipid degeneration, chemical burns, bacterial ulcers, fungal ulcers, herpes simplex infections, herpes zoster infections, protozoan infections, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, diabetic retinopathy, macular edema, macular degeneration, sickle cell anemia, sarcoid, pseudoxanthoma elasticum, Paget's disease, vein occlusion, artery occlusion, carotid obstructive disease, chronic uveitis/vitritis, Lyme disease, systemic lupus erythematosus, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, rubeosis (neovascularization of the ankle), diseases caused by the abnormal proliferation of fibrovascular or fibrous tissue including all forms of proliferative vitreoretinopathy, whether or not associated with diabetes, neovascular disease, pannus, diabetic macular edema, vascular retinopathy, retinal degeneration, inflammatory diseases of the retina, proliferative vitreoretinopathy, diseases associated with rubeosis (neovascularization of the ankle), diseases caused by the abnormal proliferation of fibrovascular or fibrous tissue including all forms of proliferative vitreoretinopathy, Crohn's disease and ulcerative colitis, sarcoidosis, osteoarthritis, inflammatory bowel diseases, skin lesions, Osler-Weber-Rendu disease, or hereditary hemorrhagic telangiectasia, osteoarthritis, Sarcoidosis, skin lesions, acquired immune deficiency syndrome, and small bowel obstruction.

The inhibition of angiogenesis in treating or reversing the disease state or condition is an important aspect of the present invention. More particularly, the present invention relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Treatment of internal malignancies such as eye or ocular cancer, rectal cancer, colon cancer, cervical cancer, prostate cancer, breast cancer and bladder cancer, among numerous others, and oral malignancies are also contemplated by the present invention.

Angiogenesis inhibiting compounds of the present invention are used to treat, ameliorate or prevent benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Angiogenesis is prominent in solid tumor formation and metastasis. Angiogeneic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention or control of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means can lead to cessation of the recurrence of the tumors.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenic disease, angiogenic disorder and angiogenic skin disorder are used throughout the specification to describe a disorder, generally a skin disorder or related disorder which occurs as a consequence of or which results in increased vascularization in tissue. Any skin disorder which has as a primary or secondary characterization, increased vascularization, is considered an angiogenic skin disorder for purposes of the present invention and is amenable to treatment with compounds according to the present invention.

Methods for treating, ameliorating, or preventing angiogenic skin disorders such as psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

Diseases associated with neovascularization include optic disc neovascularization, iris neovascularization, retinal neovascularization, choroidal neovascularization, corneal neovascularization, and intravitreal neovascularization.

Diseases associated with corneal neovascularization and retinal/choroidal neovascularization that can be treated, ameliorated, or prevented, according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, *Mycobacteria* infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratomy, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle), diseases caused by the abnormal proliferation of fibrovascular or fibrous tissue including all forms of proliferative vitreoretinopathy, whether or not associated with diabetes, and corneal graft rejection.

In some embodiments, the corneal neovascularization to be treated or inhibited is caused by trauma, chemical burns or corneal transplantation. In other particular embodiments, the iris neovascularization to be treated or inhibited is caused by diabetic retinopathy, vein occlusion, ocular tumor or retinal detachment. In still other particular embodiments, the retinal or intravitreal neovascularization to be treated or inhibited is caused by diabetic retinopathy, vein occlusion, sickle cell retinopathy, retinopathy of prematurity, retinal detachment, ocular ischemia or trauma. Additional diseases associated with choroidal neovascularization to be treated or inhibited are caused by retinal or subretinal disorders of age-related macular degeneration, diabetic macular edema, presumed ocular histoplasmosis syndrome, myopic degeneration, angioid streaks or ocular trauma.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium.

Diseases associated with chronic inflammation and arthritis can be treated, ameliorated or prevented by the compositions and methods of the present invention. Diseases with symptoms of chronic inflammation include inflammatory bowel diseases such as Crohn's disease and ulcerative colitis, psoriasis, sarcoidosis, rheumatoid arthritis, osteoarthritis, lupus and scleroderma. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state.

The compositions and methods of the present invention can be used to treat, ameliorate or prevent disease in patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease is active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease (or symptoms thereof) which can be treated, ameliorated or prevented according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are Osler-Weber-Rendu disease, or hereditary hemorrhagic telangiectasia, and acquired immune deficiency syndrome.

Factors associated with angiogenesis may also have a role in osteoarthritis. The activation of the chondrocytes by angiogeneic-related factors contributes to the destruction of the joint. At a later stage, the angiogeneic factors would promote new bone formation. Therapeutic intervention that prevents the bone destruction could halt the progress of the disease and provide relief for persons suffering with arthritis.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula, thereby preventing conception.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

The present compounds may be used to treat subjects including animals, and in particular, mammals, including humans, as patients. Thus, humans and other animals, and in particular, mammals, suffering from diseases or disorders related to angiogenesis, can be treated, ameliorated or prevented by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional therapies, e.g., cancer therapy, such as radiation treatment or surgery.

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

While the angiogenesis inhibiting compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The angiogenesis inhibiting compounds of the present invention may be administered orally, parenterally, by inhalation spray, rectally, vaginally, or topically in dosage unit formulations containing conventional pharmaceutically acceptable carriers, adjuvants, and vehicles. The term parenteral as used herein includes, subcutaneous, intravenous, intramuscular, intrasternal, infusion techniques, intraperitoneally, eye or ocular, intrabuccal, transdermal, intranasal, into the brain, including intracranial and intradural, into the joints, including ankles, knees, hips, shoulders, elbows, wrists, directly into tumors, and the like, and in suppository form.

The pharmaceutically active compounds of this invention can be processed in accordance with conventional methods of pharmacy to produce medicinal agents for administration to patients, including humans and other mammals.

Modifications of the active compound can affect the solubility, bioavailability and rate of metabolism of the active species, thus providing control over the delivery of the active species. Further, the modifications can affect the anti-angiogenesis activity of the compound, in some cases increasing the activity over the parent compound. This can easily be assessed by preparing the derivative and testing its activity according to known methods well within the routineer's skill in the art.

Pharmaceutical compositions based upon these chemical compounds comprise the above-described compounds in a therapeutically effective amount for treating diseases and conditions which have been described herein, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued US patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

A skilled artisan will recognize that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The angiogenesis-inhibiting compound may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

More specifically, the angiogenesis-inhibiting compound is administered through an ocular device suitable for direct implantation into the vitreous of the eye. Such devices of the present invention are surprisingly found to provide sustained controlled release of various compositions to treat the eye without risk of detrimental local and systemic side effects. An object of the present ocular method of delivery is to maximize the amount of drug contained in an intraocular device while minimizing its size in order to prolong the duration of the implant. See, e.g., U.S. Pat. Nos. 5,378,475; 5,773,019; 6,001,386; 6,217,895, 6,375,972, and 6,756,058 and U.S. Publications 20050096290 and 200501269448.

Other methods of delivery include: an ocular delivery system that could be applied to an intra-ocular lens to prevent inflammation or posterior capsular opacification, an ocular delivery system that could be inserted directly into the vitreous, under the retina, or onto the sclera, and wherein inserting can be achieved by injecting the system or surgically implanting the system, a sustained release drug delivery system, and a method for providing controlled and sustained administration of an agent effective in obtaining a desired local or systemic physiological or pharmacological effect comprising surgically implanting a sustained release drug delivery system at a desired location.

Examples include, but are not limited to the following: a sustained release drug delivery system comprising an inner reservoir comprising an effective amount of an agent effective in obtaining a desired local or systemic physiological or pharmacological effect, an inner tube impermeable to the passage of said agent, said inner tube having first and second ends and covering at least a portion of said inner reservoir, said inner tube sized and formed of a material so that said inner tube is capable of supporting its own weight, an impermeable member positioned at said inner tube first end, said impermeable member preventing passage of said agent out of said reservoir through said inner tube first end, and a permeable member positioned at said inner tube second end, said permeable member allowing diffusion of said agent out of said reservoir through said inner tube second end; a method for administering a compound of the invention to a segment of an eye, the method comprising the step of implanting a sustained release device to deliver the compound of the invention to the vitreous of the eye or an implantable, sustained release device for administering a compound of the invention to a segment of an eye; a sustained release drug delivery device comprising: a) a drug core comprising a therapeutically effective amount of at least one first agent effective in obtaining a diagnostic effect or effective in obtaining a desired local or systemic physiological or pharmacological effect; b) at least one unitary cup essentially impermeable to the passage of said agent that surrounds and defines an internal compartment to accept said drug core, said unitary cup comprising an open top end with at least one recessed groove around at least some portion of said open top end of said unitary cup; c) a permeable plug which is permeable to the passage of said agent, said permeable plug is positioned at said open top end of said unitary cup wherein said groove interacts with said permeable plug holding it in position and closing said open top end, said permeable plug allowing passage of said agent out of said drug core, through said permeable plug, and out said open top end of said unitary cup; and d) at least one second agent effective in obtaining a diagnostic effect or effective in obtaining a desired local or systemic physiological or pharmacological effect; or a sustained release drug delivery device comprising: an inner core comprising an effective amount of an agent having a desired solubility and a polymer coating layer, the polymer layer being permeable to the agent, wherein the polymer coating layer completely covers the inner core.

The methods are particularly suitable for treating ocular conditions such as glaucoma, proliferative vitreoretinopathy, macular edema, including diabetic macular edema, age-related macular degeneration, diabetic retinopathy, uveitis, ocular neovascularization, and ocular infection. The devices are also particularly suitable for use as an ocular device in treating subjects suffering from ocular histoplasmosis, wherein the device is surgically implanted within the vitreous of the eye.

The angiogenesis-inhibiting compound may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prodnisone, dexamethasone), non-steroidal anti-inflammatory drugs (NSAIDS) (e.g., ibuprofen, celecoxib, aspirin, indomethicin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® and Rituxan®. Other known anti-cancer agents which can be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

The active compound or pharmaceutically acceptable salts thereof can also be mixed with other active materials that do not impair the desired action, or with materials that supplement the desired action, such as other anticancer agents, and in certain instances depending upon the desired therapy or target, antibiotics, antifungals, antiinflammatories, antiviral compounds or other agents having a distinct pharmacological effect.

Alternatively, the compound of the invention may be administered apart from the at least one known cancer chemotherapeutic agent. In one embodiment, the compound of the invention and the at least one known cancer chemotherapeutic agent are administered substantially simultaneously, i.e., the compounds are administered at the same time or one after the other, so long as the compounds reach therapeutic levels in the blood at the same time. On another embodiment, the compound of the invention and the at least one known cancer chemotherapeutic agent are administered according to their individual dose schedule, so long as the compounds reach therapeutic levels in the blood.

It should be understood that in addition to the ingredients particularly mentioned above, the formulations of the present invention may include other agents conventional in the art having regard to the type of formulation in question, for example, those suitable for oral administration may include flavoring agents.

In certain pharmaceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214. The prodrug forms may be active themselves, or may be those such that when metabolized after administration provide the active therapeutic agent in vivo.

Pharmaceutically acceptable salt forms may be the preferred chemical form of compounds according to the present invention for inclusion in pharmaceutical compositions according to the present invention.

Certain of the compounds, in pharmaceutical dosage form, may be used as agents for preventing a disease or condition from manifesting itself. In certain pharmaceutical dosage forms, the pro-drug form of the compounds according to the present invention may be preferred. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including pro-drug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Preferred unit dosage formulations are those containing a daily dose or unit, daily sub-dose, as hereinabove recited, or an appropriate fraction thereof, of the administered ingredient.

The dosage regimen for treating a disorder or a disease with the angiogenesis inhibiting compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject will depend on a number of factors, such as the mode of administration, the nature of the condition being treated, the body weight of the subject being treated and the judgment of the prescribing physician.

The amount of compound included within therapeutically active formulations according to the present invention is an effective amount for treating the infection or condition. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. In some aspects, a therapeutically effective amount of a compound of the invention in a dosage form may be a therapeutically effective low dose in the range of less than about 0.001 mg/kg/day to about 10 mg/kg/day, preferably about 0.025 mg/kg/day to about 1 mg/kg/day of the patient or considerably less, depending upon the compound used, the condition or infection treated and the route of administration. The dosage of the compound will depend on the condition being treated, the particular compound, and other clinical factors such as weight and condition of the patient and the route of administration of the compound. It is to be understood that the present invention has application for both human and veterinary use.

For oral administration to humans, a dosage of between approximately 0.1 to 100 mg/kg/day, preferably between approximately 1 and 100 mg/kg/day, is generally sufficient.

Where drug delivery is systemic rather than topical, this dosage range generally produces effective blood level concentrations of active compound ranging from less than about 0.04 to about 400 micrograms/cc or more of blood in the patient.

The compound is conveniently administered in any suitable unit dosage form, including but not limited to one containing 1 to 3000 mg, preferably 5 to 500 mg of active ingredient per unit dosage form. An oral dosage of 10-250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In certain embodiments, the compound is administered once daily; in other embodiments, the compound is administered twice daily; in yet other embodiments, the compound is administered once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compounds of the invention can be used to treat diseases and disease conditions that are acute, and may also be used for treatment of chronic conditions. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

Still other objects, features, and attendant advantages of the present invention will become apparent to those skilled in the art from a reading of the preceding detailed description of embodiments constructed in accordance therewith, taken in conjunction with the accompanying drawings.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed on conjunction with other therapeutic compounds.

The invention also provides kits for treatment or prevention of a disease or disorder (or symptoms) thereof associated with angiogenesis. In one embodiment, the kit includes an effective amount of an angiogenesis-inhibiting compound in unit dosage form, together with instructions for administering the angiogenesis-inhibiting compound to a subject suffering from or susceptible to a disease or disorder or symptoms thereof associated with angiogenesis, wherein the effective amount of an angiogenesis-inhibiting compound is less than 500 mg of the compound. In preferred embodiments, the kit comprises a sterile container which contains the angiogenesis-inhibiting compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the angiogenesis-inhibiting compound for treatment of a disease or disorder or symptoms thereof associated with angiogenesis; in preferred embodiments, the instructions include at least one of the following: description of the angiogenesis-inhibiting compound; dosage schedule and administration for treatment of a disease or disorder or symptoms thereof associated with angiogenesis; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples are intended to illustrate but not limit the invention.

EXAMPLE 1

Synthesis of Cis-Itraconazole and Azalanstat

General Experimental

Thin-layer chromatography was performed on Merck pre-coated silica gel 60F-254 plates and were visualized using 254 nm UV light, or by staining with iodine, or eerie ammonium molybdate stain. Silica gel (200-400 mesh, Merck) was used for flash chromatography. Reagents were purchased from Aldrich, Acros, or Lancaster companies. Melting points were recorded on a MeI-Temp II apparatus and are uncorrected. NMR data were collected on a Varian Unity-400 (400 MHz $^1$H, 100 MHz $^{13}$C) machine at the Department of Pharmacology and Molecular Sciences, The Johns Hopkins University. $^1$H NMR spectra were obtained in deuteriochloroform (CDCl$_3$) with tetramethylsilane (TMS, $\delta$=0.00 for $^1$H) or chloroform ($\delta$=7.27 for $^1$H), or dimethylsulfoxide-d$_6$ with tetramethylsilane (TMS, $\delta$=0.00 for $^1$H) as an internal reference. $^{13}$C NMR spectra were proton decoupled and were either in CDCl$_3$ with either TMS ($\delta$=0.0 for $^{13}$C) or chloroform ($\delta$=77.0 for $^{13}$C), or dimethylsulfoxide-d$_6$ with tetramethylsilane (TMS, $\delta$=0.00 for $^1$H) as an internal reference. Chemical shifts are reported in ppm ($\delta$); multiplicities are indicated by s (singlet), d (doublet), t (triplet), q (quartet), m (multiplet), dd (doublet of doublet), dt (doublet of triplet), br. (broad), app. (apparent) and exch. (exchangeable); coupling constants, J, are reported in Hertz (Hz); integration is provided; Data are presented in the form: chemical shift (multiplicity, coupling constants, integration and assignments where relevant). Low-resolution mass spectra were obtained on a Voyager DE-STR, MALDI-TOF instrument at the AB Mass Spectrometry/Proteomics Facility at the Johns Hopkins University. The MALDI-samples were prepared by mixing droplets of the sample solutions in chloroform or methanol and 2,5-dihydroxybenzoic acid solution in acetone, where the latter served as the matrix. Data are reported in the form m/z (intensity relative to base=100). High-resolution mass spectra were acquired on a VG Instruments 70-S MS at the Chemistry Department of Johns Hopkins University. The solvents used in reactions were reagent grade. The solvents used for extraction and chromatography were technical grade. All nonaqueous reactions were performed in oven-dried glassware.

Abbreviations:

TfOH: trifluoromethanesulfonic acid;

DBU: 1,8-Diazabicyclo[5.4.0]undec-7-ene

Synthesis of 4S/R-Cis-Itraconazole Stereoisomers

1-(2,4-Dichlorophenyl)-2-(1H-1,2,4-triazol-1-yl)ethanone (2)[33]

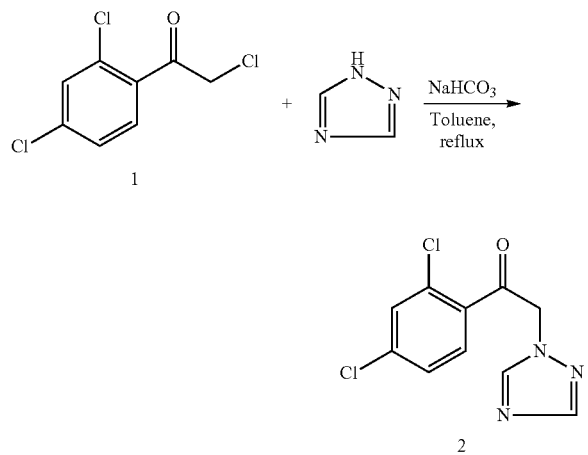

To a suspension containing 13.8 g of 1H-1,2,4-triazole and 8.4 g of NaHCO₃ in 100 mL toluene, 22.4 g of 2-chloro-2',4'-dichlorophenylacetone (1) was added. The reaction mixture was heated to 100° C. for 3 h and then cooled to −20° C. overnight. The mixture was filtered to get the yellowish solid. Then the collected solid was added to 200 mL water and extracted with EtOAc (3×150 mL). The organic layer was washed with brine and dried (MgSO₄). The solvent was removed and the solid was washed with EtOAc/hexanes (1:1, 100 mL) to get ketone 2 (13.5 g 52.6%).

MP: 160-161° C.

$^1$H NMR (400 MHz, CDCl₃): δ 8.24 (s, 1H), 7.97 (s, 1H), 7.64 (d, J=7.2 Hz, 1H), 7.50 (d, J=2 Hz, 1H), 7.38 (dd, J$_1$=2 Hz, J$_2$=8.4 Hz, 1H), 5.64 (s, 2H)

MALDI-MS: 256.1 (M+H⁺), 258.1, 278.1 (M+Na⁺), 280.1.

((2S,4S)-2-((1H-1,2,4-Triazol-1-yl)methyl)-2-(2,4-dichlorophenyl)-1,3-dioxolan-4-yl)methyl 4-methylbenzenesulfonate (3a)

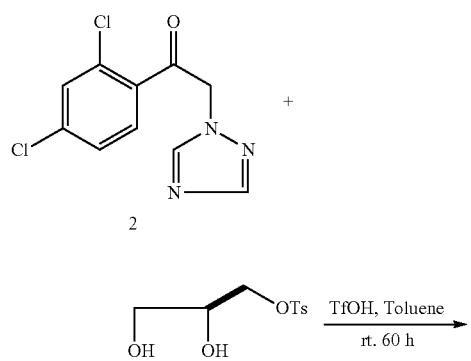

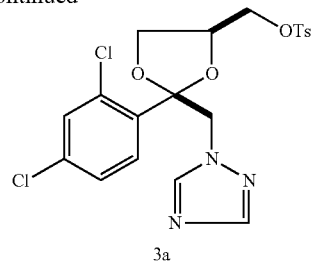

Under an atmosphere of argon, TfOH (1.5 mL, 16 mmol) was added to a solution of (S)-1-tosyloxy-2,3-propanediol (1 g, 4 mmol) and ketone 2 (1 g, 3.9 mmol) in toluene (10 mL). Then the reaction mixture was stirred at room temperature for 60 h. The reaction was quenched by adding saturated aqueous NaHCO₃ (25 mL), then extracted with EtOAc (3×30 mL), washed with brine and dried over MgSO₄. The solvent was removed and the residue was re-dissolved in 2 mL EtOAc. 4-Toluenesulfonic acid monohydrate (750 mg, 3.9 mmol) in EtOAc (2 mL) was added dropwise to precipitate 3a preferentially as a white solid. The mixture was stirred for 30 minutes and then filtered to obtain salt 3a which was recrystallized from acetonitrile to render it pure from the contaminating trans diastereomer (1.44 g, 54.6%).

MP: 181-184° C.

$^1$H NMR (400 MHz, DMSO-d6): δ 8.33 (s, 1H), 7.82 (d, J=8.4 Hz, 1H), 7.66 (d, J=2.4 Hz, 1H), 7.52 (d, J=8.0 Hz, 2H), 7.47 (d, J=8.0 Hz, 2H), 7.32-7.40 (m, 2H), 7.11 (d, J=8.0 Hz, 2H), 4.73 (s, 2H), 4.20-4.26 (m, 1H), 3.94 (dd, J$_1$=4.0 Hz, J$_2$=10.8 Hz, 1H), 3.74-3.82 (m, 2H), 3.63 (dd, J$_1$=5.6 Hz, J$_2$=8.8 Hz, 1H), 2.44 (s, 3H), 2.29 (s, 3H).

MALDI-MS: 484.1 (M+H⁺), 486.1, 506.1 (M+Na⁺), 508.1.

((2R,4R)-2-(1H-1,2,4-triazol-1-yl)methyl)-2-(2,4-dichlorophenyl)-1,3-dioxolan-4-yl)methyl 4-methylbenzenesulfonate (3b)[33]

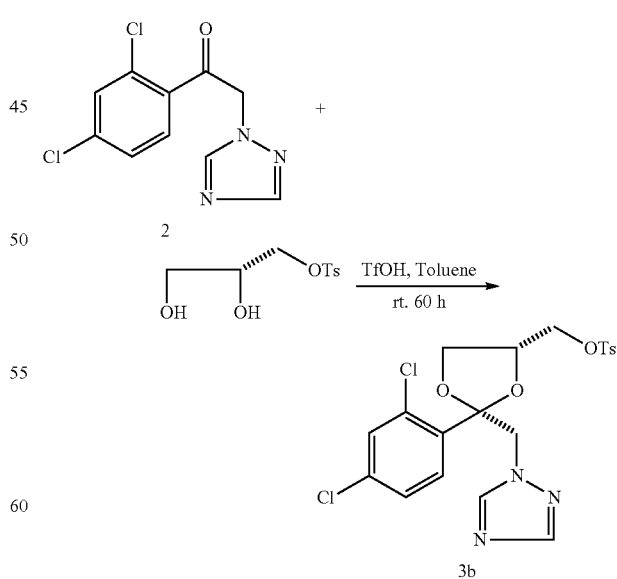

This compound was prepared from (R)-1-tosyloxy-2,3-propanediol and ketone 2 following the procedure described above for making 3a.

MP: 184-186° C.

To a solution of piperazine 4 (8 g, 41.6 mmol) and nitrobenzene 5 (6.3 g, 40.0 mmol) in DMSO (80 mL), potassium carbonate (6 g, 43.5 mmol) was added and the reaction mixture was heated at 160° C. overnight, and then cooled to room temperature. A red solid crystallized which was filtered and washed with hot ethanol to get piperazine 6. (12 g, 96% yield).

MP: 189-190° C.

$^1$H NMR (400 MHz, CDCl$_3$): δ 8.16 (d, J=9.2 Hz, 4H), 6.87-6.97 (m, 4H), 3.80 (s, 3H), 3.58-3.60 (m, 4H), 3.22-3.24 (m, 4H).

MALDI-MS: 314.1 (M+H$^+$), 336.1 (M+Na$^+$).

4-(4-(4-Methoxyphenyl)piperazin-1-yl)-aniline (7)[34]

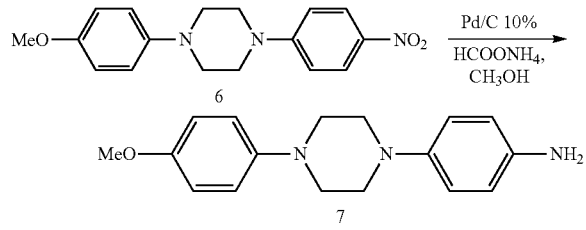

To a stirred suspension of compound 6 (9.5 g, 30 mmol) and palladium catalyst (10% Pd on carbon 0.96 g) in methanol (100 mL), ammonium formate (20 g, 317 mmol) was added slowly and the reaction mixture was heated to reflux for 3 h. After cooling to room temperature, the mixture was filtered and the filtrate was concentrated. The residue was dissolved in water (50 mL) and extracted with dichloromethane (3×40 mL). The organic layers were combined, washed (brine), dried (MgS0$_4$), and the solvent was removed to get aniline 7 (5.1 g, 60% yield).

MP: 175-180° C. (Dec.)

Phenyl 4-(4-(4-methoxyphenyl)piperazin-1-yl)phenylcarbamate (8)[40]

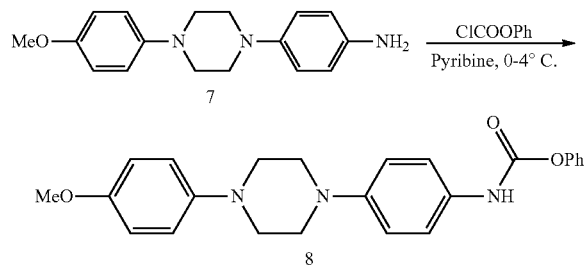

To a solution of 7 (5.13 g, 1.8 mmol) and pyridine (12 mL, 145.2 mmol) in dichloromethane (50 mL), phenyl chloroformate (5 mL, 40.9 mmol) was added at 0° C. The reaction mixture was stirred at 4° C. overnight. Then water (100 mL) was added and the mixture was stirred for 30 min. The precipitated white solid was filtered and the solid was washed with dichloromethane (2×10 mL) and then dried under vacuum to obtain carbamate 8 (5.5 g, 75% yield).

MP: 184-188° C. (Dec).

$^1$H NMR (400 MHz, CDCl$_3$): δ 7.32-7.43 (m, 4H), 7.16-7.26 (m, 3H), 6.97 (d, J=8.4 Hz, 4H), 6.87 (d, J=8.8 Hz, 2H), 6.81 (s, 1H), 3.79 (s, 3H), 3.31 (s, 4H), 3.24 (s, 4H).

MALDI-MS: 404.1 (M+H$^+$), 426.1 (M+Na$^+$).

(±)-N'-(2-butyl)formohydrazide (8a)

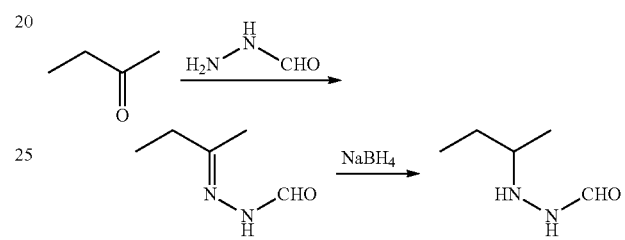

This compound was prepared following a procedure reported for the synthesis of closely related formohydrazide. To a solution of 2-butanone (1.5 g, 20.8 mmol) in tetrahydrofuran (20 mL) was added formohydrazide (1.2 g, 20 mmol) and anhydrous sodium sulfate. The flask was fitted with a Dean-Stark trap and heated to reflux for 2 hours. The reaction was cooled to room temperature and the solvent was removed to get hydrazide 8a as a white solid which was used in the reduction step directly without further purification.

The crude N'-(butan-2-ylidene)formohydrazide was dissolved in methanol (20 mL). Sodium borohydride (600 mg, 15.8 mmol) was added in portions at 0° C. The reaction was stirred at room temperature for 3.5 h. Then the solvent was removed and the residue was dissolved in water (20 mL) and extracted with dichloromethane (3×20 mL). The organic layers was combined, washed with brine and dried over MgSO$_4$. Then, the solvent was removed and the residue was purified by flash chromatography (eluent: EtOAc/hexanes=1:1) to obtain product 8a as a thick oil (1.67 g, 72% yield over two steps).

$^1$H NMR (400 MHz, CDCl$_3$): δ 7.71-7.79 (m, 1H), 4.64 (br s, 1H), 3.77 (br s, 1H), 1.44-1.60 (m, 1H), 1.24-1.38 (m, 2H), 1.05 (dd, J$_1$=2 Hz, J$_2$=4 Hz, 3H), 0.92 (td, J$_1$=3.2 Hz, J$_2$=7.6 Hz, 3H).

(±)-2-(sec-Butyl)-4-(4-(4-(4-methoxyphenyl)piperazin-1-yl)phenyl)-2H-1,2,4-triazol-3(4H)-one (9)[40]

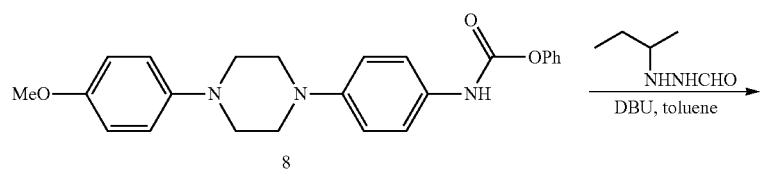

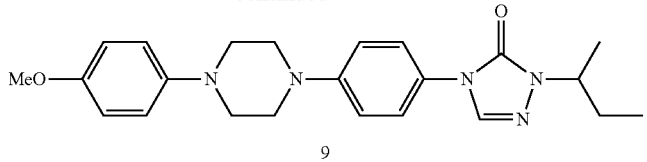

9

To a solution containing 8 (2.1 g, 5 mmol) and N'-sec-butylformohydrazide (8a) (0.72 g, 5.5 mmol) in toluene (25 mL), DBU (7.2 mg, 0.05 mmol) was added. The reaction mixture was stirred and heated at 80° C. for 7.5 h. followed by another reflux for 8 h. After cooling to room temperature, the reaction mixture was concentrated under reduced pressure, and methanol (8 mL) was added to the residue and the mixture was stirred at 4° C. for 2 hours. Filtration of the mixture gave triazolone 9 as a white solid (1.85 g, 89% yield)

MP: 189-191° C.

$^1$H NMR (400 MHz, CDCl$_3$): δ 7.62 (s, 1H), 7.43 (d, J=8.8 Hz, 2H), 7.03 (d, J=8.8 Hz, 2H), 6.97 (d, J=9.2 Hz, 2H), 6.87 (d, J=9.2 Hz, 2H), 4.25-4.34 (m, 1H), 3.35-3.38 (m, 4H), 3.22-3.25 (m, 4H), 1.66-1.92 (m, 2H), 1.39 (d, J=6.8 Hz, 3H), 0.91 (t, J=7.2 Hz, 3H).

MALDI-MS: 408.3 (M+H$^+$).

(±)-2-sec-Butyl-4-(4-(4-(4-hydroxyphenyl)piperazin-1-yl)phenyl)-2H-1,2,4-triazol-3(4H)-one (21)[40]

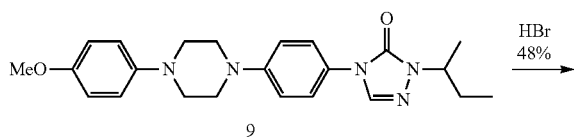

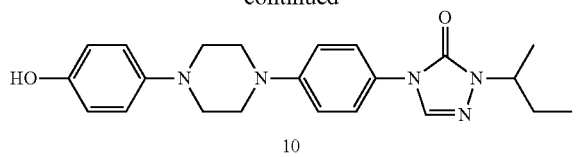

10

Triazolone 9 (0.50 g, 1.2 mmol) was added to HBr (48%, 5 mL). The reaction mixture was heated to 120° C. and refluxed overnight. The reaction mixture was cooled to room temperature, while a pink solid precipitated. The solid was collected by filtration, dissolved in methanol-water (1:1, 40 mL), saturated aqueous NaHCO$_3$ (20 mL) was added, and extracted with chloroform (3×20 mL). The organic layer was washed with brine and dried over MgSO$_4$. The solvent was removed to obtain phenol 10 (0.48 g, 98% yield).

MP: 76-78° C.

$^1$H NMR (400 MHz, CDCl$_3$): δ 7.63 (s, 1H), 7.39 (d, J=8.8 Hz, 2H), 7.00 (d, J=9.2 Hz, 2H), 6.85 (d, J=8.8 Hz, 2H), 6.72 (d, J=8.8 Hz, 2H), 5.74 (br s, 1H), 4.26-4.35 (m, 1H), 3.32-3.40 (m, 4H), 3.18-3.25 (m, 4H), 1.65-1.91 (m, 2H), 1.41 (d, J=6.8 Hz, 3H), 0.91 (t, J=7.2 Hz, 3H).

MALDI-MS: 394.3 (M+H$^+$), 416.3 (M+Na$^+$).

4-(4-(4-(4-(((2S,4R)-2-((1H-1,2,4-Triazol-1-yl)methyl)-2-(2,4-dichlorophenyl)-1,3-dioxolan-4-yl)methoxy)phenyl)piperazin-1-yl)phenyl)-2-sec-butyl-2H-1,2,4-triazol-3(4H)-one (11a)[36]

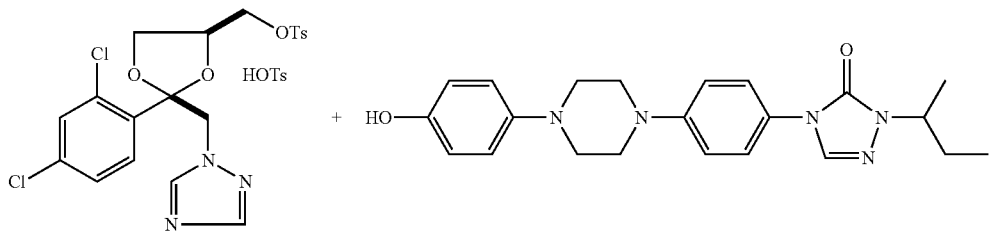

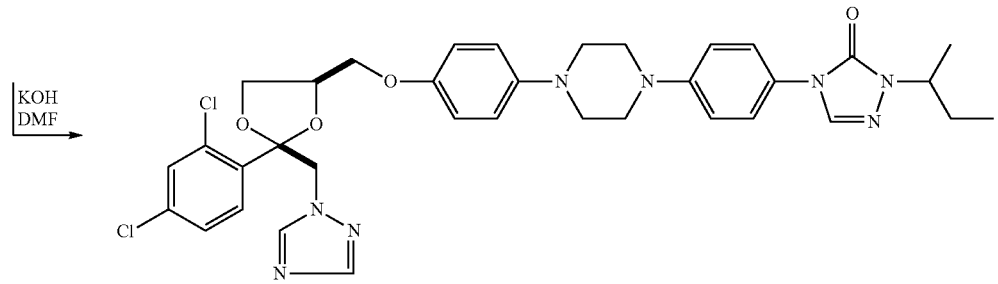

11a

To a solution of tosylate 3a (260 mg, 0.39 mmol) and phenol 10 (140 mg, 0.36 mmol) in dry DMF (5 mL) potassium hydroxide (80 mg, 1.4 mmol) was added and the reaction mixture was heated at 50° C. overnight. After cooling to room temperature, the reaction mixture was diluted with water (20 mL) and dichloromethane (20 mL), and the organic phase was separated. The aqueous phase was extracted with dichloromethane (2×20 mL). All the organic layers were combined, washed with brine (20 mL), dried (MgSO$_4$), filtered, concentrated and purified by flash chromatography on silica gel (eluent: from 1:1 EtOAc/hexanes to neat EtOAc), affording (2S,4R)-itraconazole (11a) (113 mg, 45% yield).

MP: 110-112° C.

$^1$H NMR (400 MHz, CDCl$_3$): δ 8.22 (br s, 1H), 7.90 (br s, 1H), 7.62 (s, 1H), 7.57 (d, J=8.8 Hz, 1H), 7.46 (d, J=2.0 Hz, 1H), 7.42 (d, J=9.2 Hz, 2H), 7.25 (dd, J=2.4 Hz, J$_2$=8.4 Hz, 1H), 7.02 (d, J=8.8 Hz, 2H), 6.94 (d, J=8.8 Hz, 2H), 6.79 (d, J=8.8 Hz, 2H), 4.80 (dd, J$_1$=10.4 Hz, J$_2$=34.0 Hz, 2H), 4.24-4.39 (m, 2H), 3.91 (dd, J$_1$=6.8 Hz, J$_2$=8.4 Hz, 1H), 3.76-3.82 (m, 2H), 3.47 (dd, J$_1$=6.8 Hz, J$_2$=9.6 Hz, 1H), 3.34-3.40 (m, 4H), 3.20-3.24 (m, 4H), 1.66-1.76 (m, 2H), 1.38 (d, J=7.2 Hz, 3H), 0.89 (t, J=7.2 Hz, 3H).

$^{13}$C-NMR (100 MHz, CDCl$_3$), δ152.9, 152.3, 150.8, 146.2, 136.3, 134.3, 134.2, 133.4, 131.7, 129.8, 127.5, 126.2, 123.8, 118.7, 116.9, 115.5, 107.8, 74.9, 67.8, 67.7, 53.8, 52.9, 50.9, 49.4, 28.7, 19.5, 11.0.

MALDI-MS: 705.3 (M+H$^+$), 707.3, 727.3 (M+Na$^+$), 729.3.

HRMS for 11a: Calculated for C$_{35}$H$_{38}$Cl$_2$N$_8$O$_4$ (M+H)$^+$: 705.2471, found 705.2457.

4-(4-(4-(4-(((2R,4S)-2-((1H-1,2,4-Triazol-1-yl)methyl)-2-(2,4-dichlorophenyl)-1,3-dioxolan-4-yl)methoxy)phenyl)piperazin-1-yl)phenyl)-2-sec-butyl-2H-1,2,4-triazol-3(4H)-one (11b)[36]

This compound was prepared from tosylate 3b and phenol 10 following the procedure described above for the case of the diastereomeric itraconazole (11a) (11b, 44% yield).

MP: 109-111° C.

$^1$H NMR (400 MHz, CDCl$_3$): δ 8.22 (s, 1H), 7.90 (s, 1H), 7.63 (s, 1H), 7.58 (d, J=8.8 Hz, 1H), 7.48 (d, J=2.0 Hz, 1H), 7.43 (d, J=8.8 Hz, 2H), 7.26 (dd, J$_1$=2.0 Hz, J$_2$=8.4 Hz, 1H), 7.03 (d, J=9.2 Hz, 2H), 6.94 (d, J=8.8 Hz, 2H), 6.80 (d, J=8.8 Hz, 2H), 4.81 (dd, J$_1$=14.4 Hz, J$_2$=33.6 Hz, 2H), 4.24-4.39 (m, 2H), 3.92 (dd, J$_1$=6.8 Hz, J$_2$=8.4 Hz, 1H), 3.76-3.84 (m, 2H), 3.49 (dd, J$_1$=6.0 Hz, J$_2$=9.6 Hz, 1H), 3.34-3.40 (m, 4H), 3.20-3.24 (m, 4H), 1.66-1.76 (m, 2H), 1.39 (d, J=7.2 Hz, 3H), 0.91 (t, J=7.2 Hz, 3H).

$^{13}$C-NMR (CDCl$_3$), δ152.8, 152.3, 150.8, 146.2, 136.3, 134.3, 134.2, 133.4, 131.7, 129.9, 127.5, 126.1, 123.8, 118.7, 116.9, 115.5, 107.8, 74.9, 67.8, 67.7, 53.8, 52.9, 50.8, 49.6, 28.7, 19.5, 11.0.

MALDI-MS: 705.4 (M+H$^+$), 707.4, 727.4 (M+Na$^+$), 729.4.

HRMS for 23: Calculated for C$_{35}$H$_{38}$Cl$_2$N$_8$O$_4$ (M+H)$^+$: 705.2471, found 705.2456.

Synthesis of Azalanstat 4-(4-Chlorophenyl)butan-2-one (12)[37]

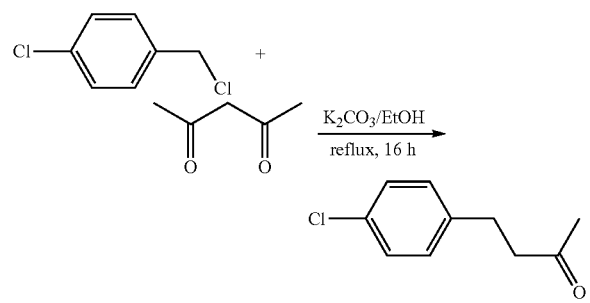

A mixture of 4-chlorobenzyl chloride (8.05 g, 55 mmol), acetylacetone (5.20 mL, 50 mmol), K$_2$CO$_3$ (6.90 g, 50 mmol), and anhydrous ethanol (50 mL) was refluxed for 16 h. The reaction mixture was cooled to room temperature and the solvent was removed. Water (100 mL) was added to the residue and the mixture was extracted with Et$_2$O (3×50 mL). The combined organic layers were washed with brine (50 mL) and dried over Na$_2$SO$_4$ and concentrated to dryness. The resulting yellow oil was distilled under reduced pressure (0.1

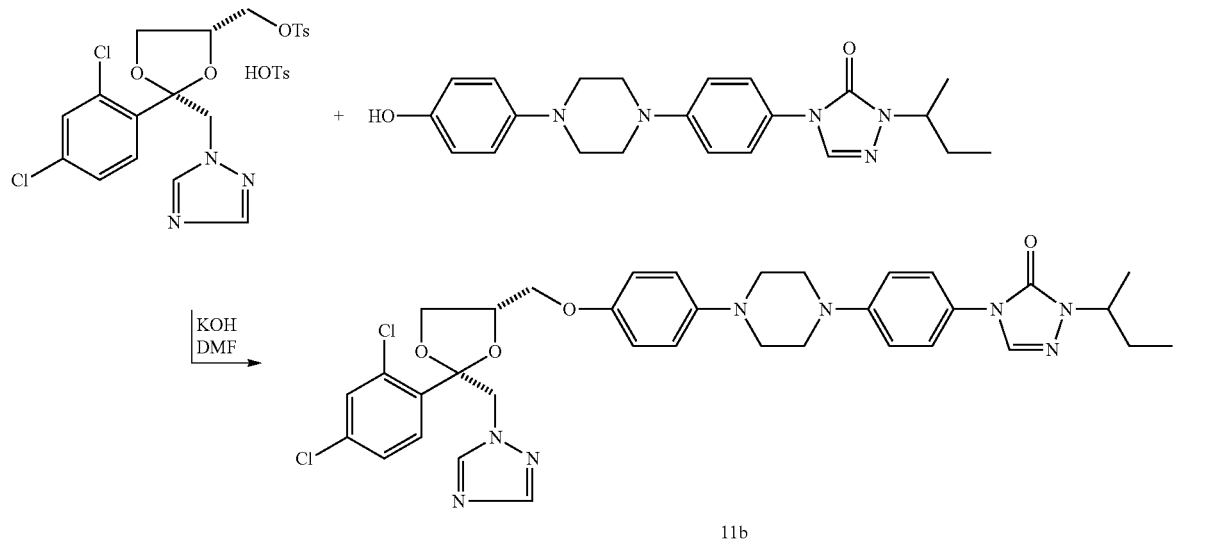

Torr) and the fraction that distilled at 110° C. was collected as a clear, colorless oil (6.15 g, 67% yield).

TLC (3:7 EtOAc/hexanes): $R_f$ 0.485.

$^1$H NMR (400 MHz, CDCl$_3$): δ 7.26-7.20 (m, 2H), 7.11-7.08 (m, 2H), 2.84 (t, J=8.0 Hz, 2H), 2.72 (t, J=8.0 Hz, 2H), 2.12 (s, 3H).

1-Bromo-4-(4-chlorophenyl)butan-2-one (13)

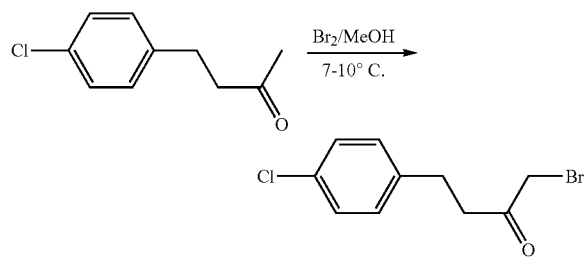

This compound was prepared following a procedure reported for making 1-bromo-4-phenyl-butan-2-one. A freshly prepared solution of bromine (910 μL, 17.74 mmol) in MeOH (15 mL) was added dropwise during 1 h 20 min to a stirred solution of benzylacetone (3.0 g, 16.42 mmol) in MeOH (15 mL) at 7-10° C. An exothermic reaction took place and to maintain the temperature at 7-10° C., the flask was immersed in an ice-water bath when necessary. Once the orange-red color of bromine disappeared, water (25 mL) was added and the mixture was stirred overnight. The organic layer was separated and the aqueous phase was extracted with CH$_2$Cl$_2$ (2×30 mL). The combined organic layers were dried over Na$_2$SO$_4$, filtered and evaporated under reduced pressure. The oily residue was dissolved in hexanes (30 mL) and the soln. was refrigerated overnight (−10° C.). Fine needles precipitated and they were filtered off, washed with cold hexanes, and dried under vacuum at room temperature to afford butanone 13 (2.76 g, 64%).

MP: 51° C.; TLC (1:4 EtOAc/hexanes): $R_f$ 0.455.

$^1$H NMR (400 MHz, CDCl$_3$): δ 7.26 (d, J=6.86 Hz, 2H), 7.13 (d, J=6.86 Hz, 2H), 3.83 (s, 2H), 3.00-2.84 (complex set of triplets, 4H).

MALDI-MS: m/z 262.2 (M+H$^+$), 286.5 (M+Na$^+$).

1-(4-(4-Chloro)phenyl-2-oxobut-1-yl)imidazole (14)$^{[39]}$

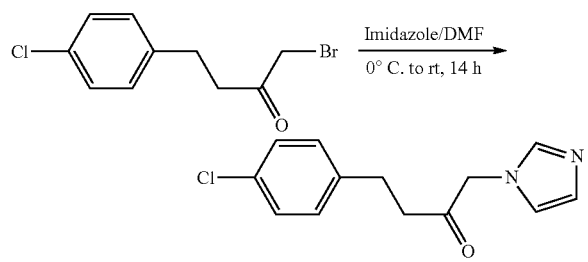

Butanone 13 (2.76 g, 10.55 mmol) was added portionwise over half an hour to a stirred suspension of imidazole (3.6 g, 53 mmol) in DMF (20 ml) at 0° C. and the mixture was stirred overnight at ambient temperature. The resulting solution was poured into water (50 mL) and the mixture was extracted with CH$_2$Cl$_2$ (3×25 mL). The organic layers were pooled and concentrated to dryness. Chromatography of the crude product on silica gel eluting with 5% methanol in CH$_2$Cl$_2$ gave imidazole derivative 14 (2.46 g, 94% yield). The hydrochloride salt crystallized from acetone/methanol (1:1) melted at 173° C.

TLC (5% MeOH/CH$_2$Cl$_2$): $R_f$ 0.351 (tailing).

$^1$H NMR (400 MHz, CDCl$_3$): δ 8.01 (s, 1H), 7.57 (d, J=4.04 Hz, 1H), 7.28-7.22 (m, 2H), 7.13-7.06 (m, 2H), 6.83 (d, J=4.04 Hz, 1H), 4.64 (s, 2H), 2.93-2.86 (m, 2H), 2.75-2.69 (m, 2H).

MALDI-MS: m/z 249.2 (MH$^+$), 271.2 (M+Na$^+$).

(2SR,4S)-2-(1-Imidazolylmethyl)-2-(2-(4-chlorophenyl)ethyl)-4-(4-methylbenzenesulfonyloxy-methyl)-1,3-dioxalane (15a and 15b)$^{[40]}$

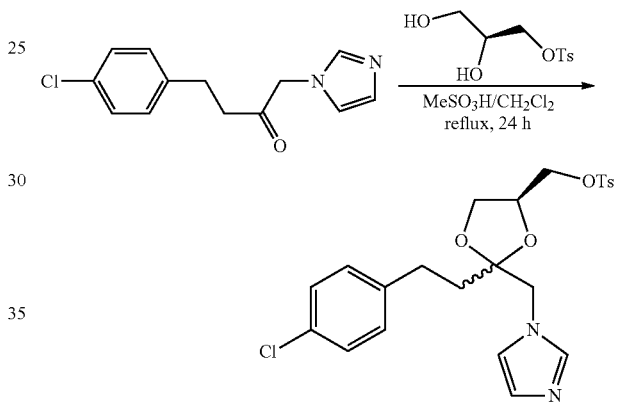

In a two-necked flask provided with a Dean-Stark trap, methanesulfonic acid (780 μL) was added slowly to a solution of butanone 14 (1.0 g, 4.02 mmol) and (2S)-2,3-dihydroxyprop-1-yl-(4-methyl)-benzenesulfonate (1.123 g, 4.56 mmol) in dichloromethane (25 mL) at room temperature. After completing the addition, the solution was heated to reflux for 24 h, cooled to room temperature, and slowly poured into a mixture of ice (20 g), water (40 mL), potassium carbonate (10 g), and dichloromethane (60 mL). The organic layer was separated, and the aqueous phase was extracted with dichloromethane (3×25 mL). The combined dichloromethane layers were dried over Na$_2$SO$_4$ and filtered, and the filtrate was evaporated under reduced pressure. The residue was purified by column chromatography on silica gel eluting with chloroform), and the diastereomeric mixture of 15a and 15b was obtained as a beige solid (1.38 g, 72% yield).

TLC (5% MeOH/CH2Cl2): Rf 0.44 (tailing).

$^1$H NMR (400 MHz, CDCl$_3$): δ 8.02 (s, 1H), 7.80-7.77 (m, 2H), 7.42 (d, J=4.04 Hz, 1H), 7.24-7.22 (m, 3H), 7.18-7.13 (m, 3H), 7.01 (d, J=4.04 Hz, 1H), 4.37-4.32 (m, 1H), 4.15-4.03 (m, 3H), 3.75-3.72 (m, 2H), 3.27-3.23 (m, 1H), 2.92-2.88 (2 s, s, 3H), 2.67-2.64 (m, 2H), 2.43-2.41 (m, 1H), 1.94-1.91 (m, 2H).

MALDI-MS: m/z 477.5 (MH$^+$), 500.3 (M+Na$^+$).

(2S/R,4S)-Azalanstat (16a and 16b)

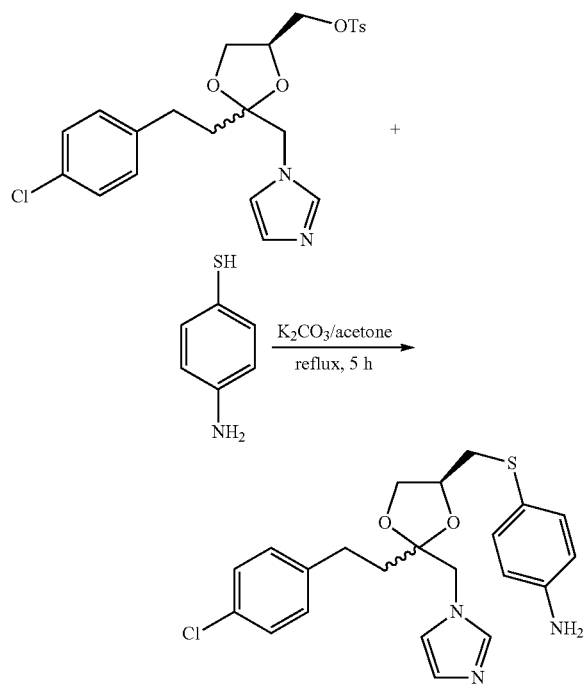

Under a $N_2$ atmosphere, a mixture of tosylate 15a and 15b (450 mg, 0.94 mmol), 4-aminothiophenol (247 mg, 1.97 mmol), and $K_2CO_3$ (260 mg, 1.88 mmol) in acetone was heated to reflux temperature with stirring for 5 hours. The solids were removed by filtration, and washed with hot acetone and then with hot EtOAc. The filtrate was concentrated, and the residue was purified by flash chromatography on silica gel (EtOAc) to give a mixture of 16a and 16b (280 mg, 69% yield as a 2:3 mixture of 2S,4S i.e. 16a and 2R,4S i.e. 16b). The beige solid was then suspended in warm 1:3 $Et_2O$/$CH_2Cl_2$ (25 mL) and allowed to stand overnight in the freezer (−20° C.). Beige crystals were collected by filtration (98.6 mg, 16a (4S,2S), MP: 151° C.) and the solution was concentrated to obtain the trans diastereomer (152.3 mg, 16b (4S, 2R)).

TLC (5% MeOH/$CH_2Cl_2$): $R_f$ 0.32 (16a), 0.19 (16b).

$^1$H NMR of 16a/16b (400 MHz, Acetone-d6): δ 8.45 (d, J=9.8 Hz, 1H), 7.62 (t, J=6.7 Hz, 2H), 7.54 (apparent d, J=7.7 Hz, 4H), 7.45 (t, J=6.7 Hz, 2H), 6.34 (apparent t, J=1.4 Hz, 2H), 4.69-4.63 (m, 1H), 4.57-4.54 (m, 1H), 4.48-4.38 (m, 1H), 4.23 (d, J=2.7 Hz) and 4.16 (d, J=2.9 Hz) together 1H, 3.73-3.66 (m, 1H), 3.58-3.45 (m, 2H), 3.36-3.24 (m, 1H), 3.16 (d, J=2.9 Hz) and 3.02 (dd, J=3.3 and 0.9 Hz) together 1H, 2.74-2.70 (m, 1H), 1.84 (d, J=3.3 Hz) and 1.62 (d, J=1.8 Hz) together 1H.

MALDI-MS: m/z 430.3 (MH$^+$).

EXAMPLE 2

4S/R-Cis-Itraconazole and Azalanstat Biological Studies

Cell Culture.

HUVEC were purchased from Cambrex Biosciences (Walkersvilie, Md.) and maintained in EGM-2 media (Cambrex) which contains VEGF, bFGF, and EGF. LPDS were purchased from Intracell. BAEC and Hela cells were maintained in DMEM media containing 10% FBS. Jurkat cells were maintained in RPMI media containing 10% FBS. In a typical experiment 5,000-10,000 cells/well in 0.2 mL EGM-2 media were allowed to adhere for 8 h and then incubated with drug for 36 h. Cells were pulsed with 1 μCi [$^3$H]-thymidine for 8 h (MP Biomedicals, 6.7 Ci/mmol), and harvested using trypsin onto glass fiber filters (Wallac, Turku, Finland). The readout was performed on a Perkin Elmer MicroBeta plate reader. Cells used were under five passages.

Human foreskin fibroblast (HFF) cells were cultured at passage 2 in DMEM low glucose, 10% fetal bovine serum, and 1% penicillin-streptomycin. Experiments were performed with 2,500 cells/well in 0.2 mL and incubated for 96 h with drug. Plates containing cells were washed once with PBS, incubated with 1 μM Calcein-AM (Molecular Probes) in PBS for 4 h, and read in a fluorescent plate reader. $IC_{50}$ values were determined using four-parameter logarithmic analysis with GraphPad Prism and are presented as mean±s.e.m. for triplicate experiments.

Endothelial cells form the inner lining of all blood vessels and constitute an essential part of new as well as pre-existing blood vessels. An endothelial cell proliferation assay was utilized to screen our clinical drug library. The screen was carried out in 96-well plates with each drug at a final concentration of 10 μM. Thus, HUVEC were incubated with drugs for 36 h and proliferation was measured by following incorporation of [3H]-thymidine for the final 8 h. The preliminary screen identified 210 existing drugs with at least 50% inhibition at 10 μM, which belong to multiple drug classes (FIG. 1a).

Itraconazole displayed quite potent and selective inhibitory activity toward endothelial cells compared to other cell types tested. For example, itraconazole has little effect on the proliferation of human foreskin fibroblasts (HFF) with an IC50 over 20 μM in comparison to HUVEC (IC50=0.16 μM) (FIG. 1b). While it potently inhibited the proliferation of bovine aortic endothelial cells (BAEC), it is much less effective against Jurkat T cells or HeLa cells.

To delineate the mechanism of inhibition of endothelial cell proliferation by itraconazole, the effect on the cell cycle progression of HUVEC by fixing and staining cells with propidium iodide followed by FACS analysis was examined. The 4S-cis diastereomer potently inhibits HUVEC cell cycle progression at the G1/S transition (FIG. 1c). Treatment of HUVEC with racemic itraconazole also led to an increase of cells in the G1 phase of the cell cycle and a corresponding decrease in cells in the S phase (data not shown). These results indicate that itraconazole inhibits HUVEC proliferation by blocking cell cycle progression in the G1 phase.

Two complementary approaches were taken to assess the relevance of 14DM in the inhibition of endothelial cell proliferation by itraconazole. First, a known potent inhibitor of human 14DM, azalanstat, was prepared and its effect on endothelial cells was compared with that of itraconazole. Similar to itraconazole, azalanstat also blocked the cell cycle progression of HUVEC (FIG. 2) and BAEC in the G1 phase of the cell cycle (FIG. 3 and Table 1), suggesting that 14DM is required for endothelial cell proliferation.

TABLE 1

Effects of itraconazole and azalanstat
on the cell cycle progression of BAEC*.

|  | Control | | | Cholesterol | | |
| --- | --- | --- | --- | --- | --- | --- |
|  | G1 | S | G2/M | G1 | S | G2/M |
| Control | 66.4 | 18.7 | 14.2 | 65.5 | 22.1 | 11.8 |
| Itraconazole | 77.0 | 10.5 | 12.0 | 66.2 | 21.2 | 12.0 |
| Azalanstat | 74.5 | 16.8 | 8.8 | 70.2 | 19.4 | 10.0 |

*Values represent the percentage of cells in a given phase of the cell cycle.

A hallmark of inhibitors of 14DM is that their potencies are dependent on the levels of cholesterol in cell culture medium. Thus, the potencies of both azalanstat and itraconazole in cell culture media either containing or lacking cholesterol was determined.

Figure 2B:
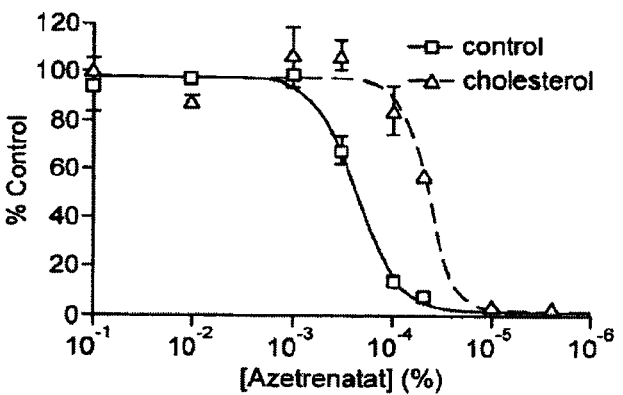

Azalanstat displayed higher potency toward endothelial cells in the absence of cholesterol ($IC_{50}$=0.31 µM) than in its presence ($IC_{50}$=1.2 µM) (FIG. 2a). Similarly, the inhibition of endothelial cells by itraconazole was also sensitive to cholesterol, being less potent when cholesterol is present ($IC_{50}$=0.044 µM vs. 0.23 µM) (FIG. 2b).

Figure 2C:
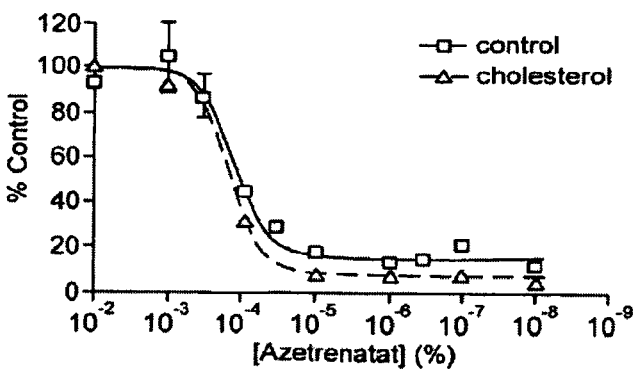

In contrast, an inhibitor of angiogenesis with unrelated mechanism of action, TNP-470, that works by inhibiting the type 2 methionine aminopeptidase, inhibited endothelial cell proliferation with roughly equal potency in the absence and presence of cholesterol (FIG. 2c).

Together, these observations suggest that itraconazole works at least in part by inhibiting cholesterol biosynthesis.

The second approach was to knockdown the expression of human 14DM in HUVEC and determine the effect on cell proliferation. Thus, three different shRNAs targeting the coding region of human 14DM mRNA were transiently expressed in 293T cells along with the expression plasmid for human 14DM with an C-terminal c-Myc tag.

Figure 3A:
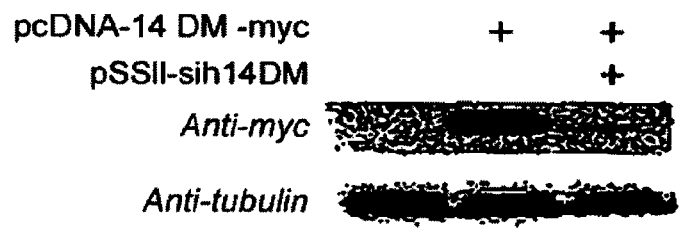
FIG. 3 shows the knockdown of 14DM in HUVEC inhibits proliferation. (a) Western blot of knockdown of transiently-expressed 14DM protein. (b) RT-PCR of 14DM knockdown HUVEC. c) Knockdown of human 14DM in HUVEC inhibits cell proliferation.

One of the constructs, pSSII-sih14DM, dramatically blocked the expression of ectopically expressed protein (FIG. 3a). The expression cassette for this shRNA was then moved to the lentiviral vector, pFUP2, and the resulting lentiviruses were generated and used to transduce HUVEC.

Figure 3B:
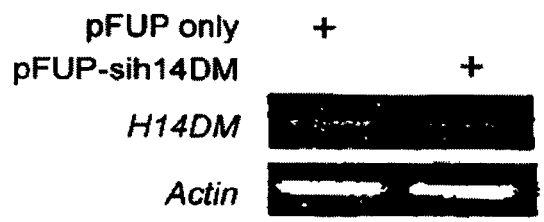

As shown in FIG. 3b, the human 14DM lentiviral shRNA blocked the expression of endogenous 14DM expression, as judged by RT-PCR about 3 days after viral transduction.

Figure 3C:
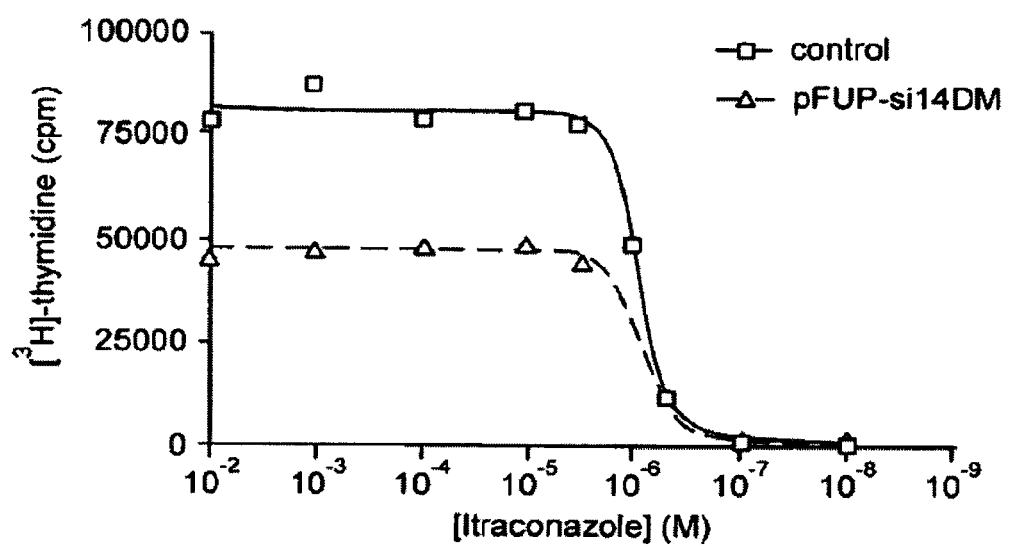

The transduced cells were allowed to grow and their proliferation in the absence and presence of varying concentrations of itraconazole was determined at days 7 and 10 post-transduction, respectively. HUVEC transducted with human 14DM shRNA proliferate more slowly than those transduced with the control viruses, as judged by the amounts of [3H]-thymidine incorporated at Day 7 (FIG. 3c).

Together, these results demonstrate that 14DM is essential for endodielial cell growth and suggest that human 14DM may serve as a novel target for developing angiogenesis inhibitors.

To determine whether itraconazole inhibited angiogenesis in vivo, itraconazole was tested in a mouse Matrigel model. In humans, itraconazole is administered intravenously at a dose of 105 mg/m$^2$ twice daily. Mice were thus treated with a comparable dose of itraconazole (112.5 mg/m2 or 37.5 mg/kg, i.p. once daily).

Female athymic nude 5-week old, 25-30 g mice were purchased from NO and treated in accordance with standard procedures. In all animal experiments the i.v. formulation of itraconazole was obtained from the Johns Hopkins Hospital Pharmacy. Control mice were treated with vehicle (40% hydroxypropyl-β-cyclodextrin, 2.5% propylene glycol, pH 4.5). Mice were pretreated for three days and then implanted subcutaneously with 0.5 mL of Matrigel (BD Biosciences) containing 100 ng/mL VEGF and 150 ng/mL bFGF. Drug treatment was continued daily for 10 days, mice were sacrificed, and plugs were harvested, fixed in neutral buffered formalin, and processed for histology using MAS-trichrome staining. A cross section of the entire Matrigel plug was photographed at 100× and erythrocyte-filled blood vessels were counted per field in a blinded manner. P-values comparing itraconazole versus vehicle treated mice were determined using the two-tailed Student's T-test; and the data are presented as mean±s.e.m.

Figure 4C:
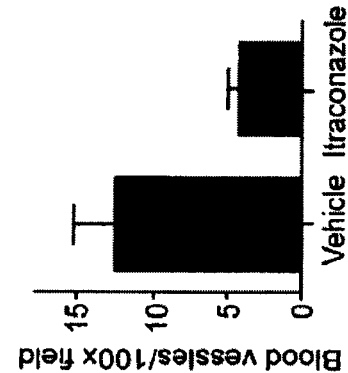
FIG. 4 shows the treatment of mice with itraconazole, 37.5 mg/kg/day, i.p. significantly inhibited angiogenesis as shown in representative Matrigel plugs (a) and in 100× sections of plugs harvested from mice (b). (c) Erythrocyte-filled blood vessels were counted per 100× field (*p=0.01, n=6 vehicle, n=8 itraconazole).
Figure 4B:
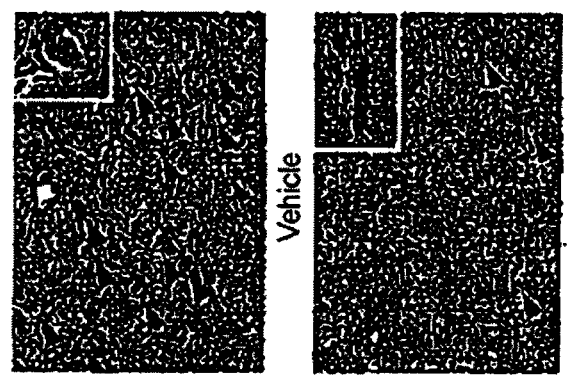
Figure 4A:
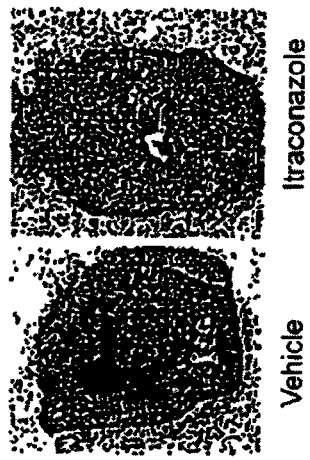
Figure 8:
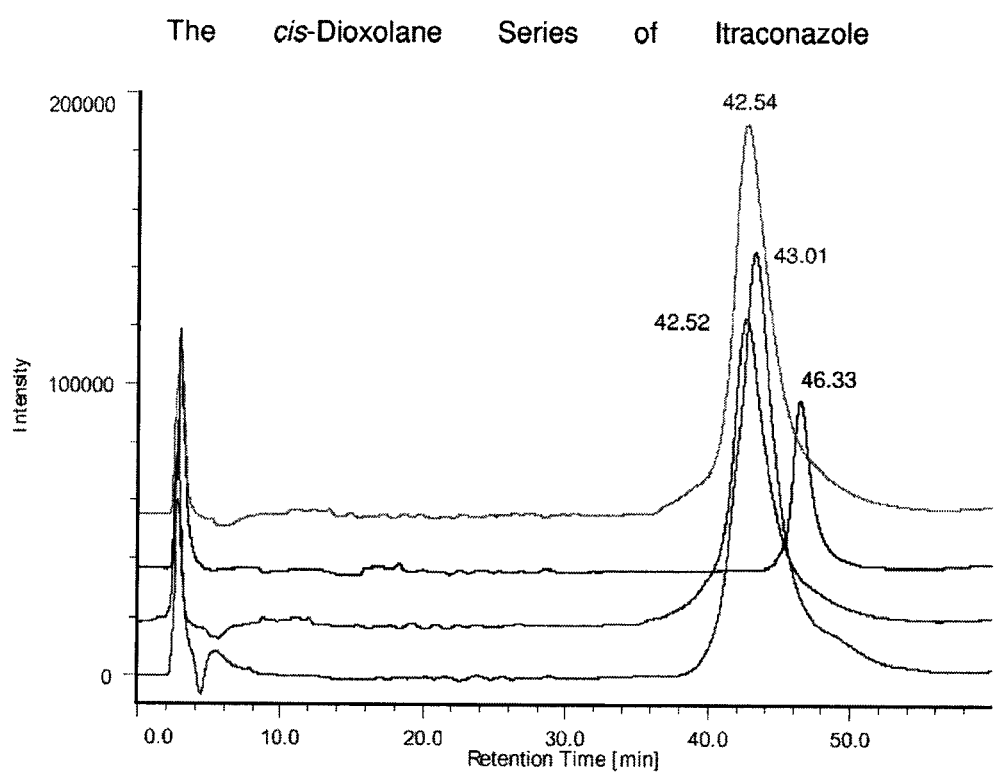
FIG. 8 shows overlayed HPLC chromatograms for the cis-dioxolane series of itraconazole. The order of the chromatograms for the stereoisomers from bottom to top is: 23a; 23d; 23b; and 23c.
Figure 9:
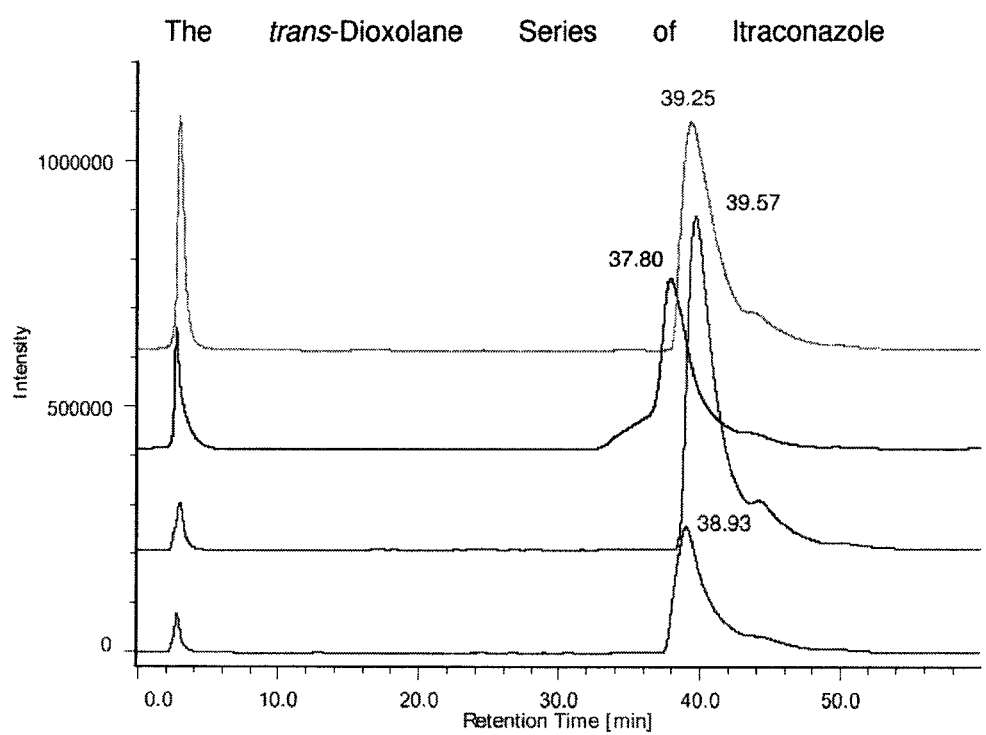
FIG. 9 shows overlayed HPLC chromatograms for the trans-dioxolane series of itraconazole. The order of the chromatograms for the stereoisomers from bottom to top is: 23e; 23h; 23f; and 23g.

A significant decrease in angiogenesis was observed both macroscopically, as judged by the red color of the isolated Matrigel plugs (FIG. 4a), and microscopically upon staining thin sections for new blood vessels (FIG. 4b) in animals treated with itraconazole. Overall, there was a 67.5% decrease in new blood vessel formation in itraconazole-treated mice compared to vehicle-treated controls (FIG. 3c), indicating itraconazole is capable of suppressing angiogenesis in vivo.

EXAMPLE 3

Itraconazole Stereoisomers

General Experimental

Reactions were carried out in oven dried glassware. All reagents were purchased from commercial sources and were used without further purification unless noted. Unless stated otherwise, all reactions were carried out under a positive pressure of argon and were monitored by Merck precoated silica gel 60F-254 plates and were visualized using 254 nm UV light. Column chromatography was performed on silica gel (200-400 mesh, Merck). The ratio between silica gel and crude product ranged from 100 to 50:1 (w/w). NMR data were collected on a Varian Unity-400 (400 MHz 1H, 100 MHz 13C) machine in the Department of Pharmacology and Molecular Sciences, the Johns Hopkins University. 1H NMR spectra were obtained in deuteriochloroform (CDCl$_3$) with either tetramethylsilane (TMS, δ=0.00 for $^1$H) or chloroform (CHCl$_3$, δ=7.27 for $^1$H) as an internal reference. $^{13}$C NMR spectra were proton decoupled and were in CDCl$_3$ with either TMS (δ=0.0 for $^{13}$C) or CHCl$_3$ (δ=77.0 for $^{13}$C) as an internal reference. Chemical shifts are reported in ppm (δ). Data are presented in the form: chemical shift (multiplicity, coupling constants, and integration). $^1$H data are reported as though they were first order. The errors between the coupling constants for two coupled protons were less than 0.5 Hz, and the average number was reported. The low-resolution mass spectra were obtained on a Voyager DE-STR, MALDI-TOF instrument at the AB Mass Spectrometry/Proteomics Facility at the Johns Hopkins University. The MALDI-samples were prepared by mixing droplets of the sample solutions in chloroform or methanol and 2,5-dihydroxybenzoic acid solution in acetone, where the latter served as the matrix. The high-resolution mass spectra were acquired on an ABI Voyager-DE STR instrument in the Department of Chemistry at the Texas A&M University. The ionization method is MALDI by using THAP (2,4,6-trihydroxyacetophenone) as the matrix. Optical rotations were measured on a Jasco P-1010 polarimeter at the sodium D line (589 nm) in the Department of Chemistry, the Johns Hopkins University. Optical rotations were measured at 22±2° C. Optical rotations are in units of deg·mL(dm·g)$^{-1}$.

Synthesis and Isolation of Itraconazole Stereosiomers

Trans-(2R,4S)-2-(2,4-dichlorophenyl)-2-(1H-1,2,4-triazol-1-ylmethyl)-4-tosyloxymethyl-1,3-dioxolane (22c) or trans-(2S,4R)-2-(2,4-dichlorophenyl)-2-(1H-1,2,4-triazol-1-ylmethyl)-4-tosyloxymethyl-1,3-dioxolane (22d)

After the salt formation with toluenesulfonic acid, the majority of tosylate salts of 22c or 22d were remained in the ethyl acetate solution, which was neutralized by washing with a saturated aqueous $K_2CO_3$ solution. The aqueous layer was then extracted with $CH_2Cl_2$ several times. The combined organic solution was dried ($Na_2SO_4$), filtered, and concentrated to yield the crude product, which was purified by column chromatography (50:1→5:1 $CH_2Cl_2$-acetone) to afford 22c or 22d as a yellowish oil: Rf 0.33 (5:1, $CH_2Cl_2$-acetone); $^1$H NMR (400 MHz, $CDCl_3$, $\delta H$) 8.11 (s, 1H), 7.85 (s, 1H), 7.60 (d, J=8.1 Hz, 2H), 7.49-7.22 (m, 4H), 7.09 (dd, J=8.5, 1.4 Hz, 1H), 4.73-4.60 (m, 2H), 4.14-3.98 (m, 1H), 3.94-3.80 (m, 3H), 3.59 (t, J=7.8 Hz, 1H), 2.43 (s, 3H); $^{13}$C NMR (100 MHz, $CDCl_3$, $\delta_C$) 151.69, 145.53, 144.96, 136.14, 134.54, 133.00, 132.32, 131.33, 130.15, 129.40, 128.03, 127.38, 108.28, 75.01, 67.69, 67.07, 54.37, 21.92.

MALDI-MS: 484.1 ($M+H^+$), 506.1 ($M+Na^+$).

Protocol for the Preparation of trans-Itraconazole 23e-23h

To a solution of 20a or 20b (22.6 mg, 0.057 mmol) in DMSO was added NaH (10.2 mg of a 60% dispersion in mineral oil, 0.26 mmol). After the mixture was stirred at 50° C. under argon for 1 h, a solution of 22c or 22d (30.0 mg, 0.062 mmol) in DMSO was added dropwise. After the addition, the temperature was increased to 90° C., and the solution was stirred under argon for another 3 h. The reaction was then quenched by the addition of a 50% aqueous NaCl solution, and the resulting mixture was extracted with $CH_2Cl_2$. The organic fractions were dried ($Na_2SO_4$), filtered, and concentrated under vacuum to yield the crude product, which was purified by column chromatography (1:1 hexanes-EtOAc→neat EtOAc) to afford trans-itraconazole (27.9 mg, 69%) as a yellowish oil, which could be further purified by a second column (neat $CH_2Cl_2$→50:1 $CH_2Cl_2$—$CH_3OH$) if necessary: Rf 0.56 (EtOAc); $^1$H NMR (400 MHz, $CDCl_3$, $\delta_H$) 8.23 (br s, 1H), 7.93 (br s, 1H), 7.65-7.55 (m, 2H), 7.49-7.38 (m, 3H), 7.19 (dd, J=8.5, 2.1 Hz, $^1$H), 7.13-6.85 (m, 4H), 6.68 (t, J=15.2 Hz, 2H), 4.76 (q, J=14.6 Hz, 2H), 4.36-4.15 (m, 2H), 4.00 (dd, J=8.2, 6.4 Hz, 1H), 3.89 (dd, J=10.0, 4.5 Hz, 1H), 3.80 (dd, J=13.9, 6.6 Hz, 2H), 3.20-3.57 (m, 8H), 1.94-1.77 (m, 1H), 1.78-1.64 (m, 1H), 1.39 (d, J=6.7 Hz, 3H), 0.89 (t, J=7.4 Hz, 3H); $^{13}$C NMR (100 MHz, $CDCl_3$, $\delta_C$) 152.22, 136.03, 135.23, 134.09, 133.21, 131.37, 129.69, 127.30, 123.79, 119.12, 117.12, 115.48, 108.05, 76.25, 67.79, 67.60, 54.66, 52.90, 51.30, 49.12, 28.66, 19.50, 11.03.

MALDI-MS: 705.3 ($M+H^+$), 727.3 ($M+Na^+$).

HPLC Analysis of Itraconazole Diastereomers 23a-23h
HPLC: JASCO PU-2089S Plus quaternary pump system
Column: CHIRALPAK® AS-RH (2.1×150 mm), 5 µm
Detector: MD-2010 Plus PDA
Conditions Itraconazole diastereomers were analyzed by HLPC. Briefly, 10 µL sample of each itraconazole diastereomer as ~1 mM solution in chloform was injected into a 7725i Rheodyne injection module. A mixture of acetonitrile and 5 mM aqueous ammonium acetate was used as the mobile phase with the flow rate of 0.2 mL/min. Initially, mobile phase composition was 70% 5 mM aqueous ammonium acetate and 30% acetonitrile, but the gradient was ramped up to 70% acetonitrile and 30% 5 mM aqueous ammonium acetate over 46 min starting at the $4^{th}$ min. In the next 5 min, eluent was changed to 20% 5 mM aqueous and 80% acetonitrile to wash off the column, and then it was switched to the original composition to get ready for the next injection cycle.

Biological Methods

Pooled HUVEC and EGM-2 bullet kits were purchased from Lonza. Powdered RPMI 1640 media with L-glutamine and without sodium bicarbonate was purchased from Gibco. Amino acids, uracil, and agar were purchased from Sigma and morpholinepropanesulfonic acid (MOPS) was purchased from Fisher. Dimethyl Sulfoxide (DMSO) was purchased from J. T. Baker. *C. glabrata* strains BG1 (*J. Infect. Dis.* 1996, 173, 425-431) and BG2 (*Genetics* 1999, 151, 979-987), *C. neoformans* H99 (*Am. J. Pathol.* 1980, 101, 177-193), *S. cerevisiae* BY4741 (MATa, ura3, his3, leu2, met15), and *C. albicans* (ATCC 10261) were used.

Cell Culture

HUVEC between passage 3 and 8 were grown in EGM-2 bullet kit media at 37° C. in a humidified environment with 5% $CO_2$ present. Fungi were maintained on YES (5 g/L yeast extract, 30 g/L glucose) agar (2%) plates supplemented with 225 mg/L adenine, histidine, leucine, uracil, and lysine at 30° C.

HUVEC Proliferation Assay

HUVEC were plated in a 96-well plate at a density of 2000 cells/well 199 µL media. After recovering overnight, cells were incubated for 24 hours with drugs added from 200× DMSO stocks. Next, cells were incubated with 0.9 µCi of [$^3$H]-thymidine for 6 h, washed once with PBS, trypsinized, and transferred to filtermats (Wallac) using a Mach III M Harvester 96 (Tomtec). The filtermats were then dried overnight. Using a 1450 Microbeta apparatus (Wallac), the amount of [$^3$H] at each position on the filtermat was determined by scintillation counting. Counts from vehicle only treated controls were used to normalize for maximum proliferation. Experiments were conducted in triplicate with multiple technical replicates for each data point. A four parameter logistic regression was used to determine $IC_{50}$ values (GraphPad Prism [v4.03]).

Fungal Susceptibility Assays

Fungi were grown overnight in 5 mL YES supplemented 225 mg/L adenine, histidine, leucine, uracil, and lysine (supplemented YES) at 30° C. with shaking. Cultures were diluted to 0.01 $OD_{600}$ in RPMI (with L-glutamine, without sodium bicarbonate) which was supplemented with 2% glucose, 225 mg/L adenine, histidine, methionine, leucine, uracil, and lysine and buffered with 165 mM MOPS to 7.0 (complete RPMI). This solution was then further diluted 190-fold in complete RPMI in 96-well plates containing test compounds in a final volume of 150 µL. When practical, the intermediate RPMI dilution was bypassed and the overnight cultures were directly diluted to the appropriate $OD_{600}$ in the RPMI solution that was added to the 96-well plates. Two-fold serial dilutions of the compounds were tested starting at 4 ug/mL with each well containing 0.125% vehicle (DMSO). The plates were incubated in a humidified environment at 30° C. with shaking for 30 hours except for experiments with *C. neoformans* which was incubated for 54 h. $Abs_{600}$ was measured using a plate reader (Bio-Tek Synergy HT) after vigorous shaking for 45 seconds to resuspend the cells. The background absorbance from noninoculated wells was subtracted and the absorbance of test wells was divided by that of wells treated with vehicle alone. The percent of remaining growth for each drug concentration was averaged over 2-3 independent experiments, each with two technical replicates, and the minimum concentration giving 80% inhibition ($MIC_{80}$) was determined.

After the quality of all stereoisomers was confirmed, the potency of each stereoisomer against HUVEC proliferation and fungal growth was determined (FIG. 7). HUVEC were incubated with drug or vehicle alone for 24 hours and then pulsed for 6 hours with [$^3$H]-thymidine, the incorporation of which was taken as a readout of cell proliferation. Inhibition of fungal growth was assayed by incubating five yeast strains with 2-fold serial dilutions of each stereoisomer for 30-60 hours depending on the strain, and then measuring the $OD_{600}$ of the culture to quantitate growth. The minimum concentration capable of inhibiting growth by 80% ($MIC_{80}$) was determined.

The influence of stereochemistry on the inhibition of HUVEC proliferation by itraconazole was minor. The difference in potency between 23a and 23f, the most and least potent stereoisomers, respectively, was only slightly greater than 4-fold. The most relevant stereochemical determinant of potency in HUVEC was the configuration of the dioxolane ring, with the cis-diastereomers exhibiting higher potency than the trans series by several fold. The cis-4R diastereomer was found to be slightly more potent than the cis-4S isomer, with correct stereochemical centers having been assigned. In contrast to HUVEC, the potency of itraconazole against fungal proliferation was highly influenced by stereochemistry (FIG. 7). A difference in potency of up to 32-fold was observed between stereoisomers in one fungal strain. In four out of five strains tested the least potent stereoisomers by a margin of at least 4- to 32-fold were two of the trans isomers, 23g and 23h. On the other hand, the other trans pair 23e and 23f were about as potent as the cis diastereomers (23a through 23d). The exception was C. neoformans in which 23e and 23f were 2-fold less potent than 23g and 23h and 32-fold less potent than the best inhibitor.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such enriched isomers, as well as racemic mixtures thereof, are intended to be included in this invention.

Although the invention has been described with reference to the above examples, it will be understood that modifications and variations are encompassed within the spirit and scope of the invention. Accordingly, the invention is limited only by the following claims.

What is claimed is:

1. A method of inhibiting angiogenesis in a subject, comprising administering to the subject an effective amount of a chirally pure compound of structural Formula A, wherein the compound is anti-angiogenic:

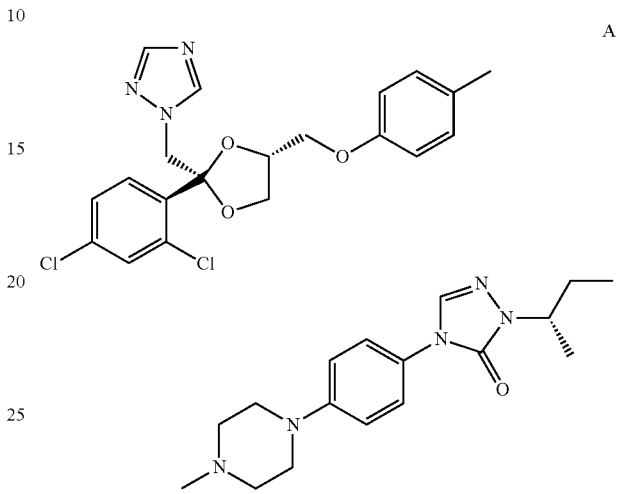

2. The method of claim 1, wherein the compound is administered at a dose of a dosage of between about 0.1 and 100 mg/kg/day.

3. The method of claim 1, wherein the administering of the anti-angiogenic compound comprises administering the compound in a dosage of less than about 500 mg/day.

4. The method of claim 1 comprising the step of administering an effective amount of a composition comprising the anti-angiogenic compound and a pharmaceutically suitable excipient.

5. The method of claim 1, wherein the administering of the anti-angiogenic compound comprises administering the compound orally, topically, parentally, intravenously or intramuscularly.

6. The method of claim 5, wherein the administration is carried out in a controlled and sustained release.

7. The method of claim 1, wherein the subject is a human.

8. The method of claim 1, wherein the compound is administered in an amount effective for treatment of retinoblastoma, cystoid macular edema (CME), macular degeneration, exudative age-related macular degeneration (AMD), diabetic retinopathy, diabetic macular edema, or ocular inflammatory disorders.

9. The method of claim 1, wherein the compound is administered in an amount effective for treatment of a disease or disorder associated with a tumor or cancer of the breast.

* * * * *